(12) United States Patent
Ware et al.

(10) Patent No.: US 10,759,863 B2
(45) Date of Patent: Sep. 1, 2020

(54) MODULATION OF γδ T CELLS

(71) Applicant: Sanford Burnham Prebys Medical Discovery Institute, La Jolla, CA (US)

(72) Inventors: Carl F. Ware, La Jolla, CA (US); John R. Sedy, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 310 days.

(21) Appl. No.: 14/916,986

(22) PCT Filed: Sep. 4, 2014

(86) PCT No.: PCT/US2014/054116
§ 371 (c)(1),
(2) Date: Mar. 4, 2016

(87) PCT Pub. No.: WO2015/035063
PCT Pub. Date: Mar. 12, 2015

(65) Prior Publication Data
US 2016/0194403 A1    Jul. 7, 2016

Related U.S. Application Data

(60) Provisional application No. 61/874,269, filed on Sep. 5, 2013.

(51) Int. Cl.
*A61K 31/7088* (2006.01)
*A61K 31/7105* (2006.01)
*A61K 38/20* (2006.01)
*C12N 15/113* (2010.01)
*C07K 16/28* (2006.01)
*G01N 33/50* (2006.01)
*A61K 45/06* (2006.01)
*A61K 31/00* (2006.01)
*C07K 14/54* (2006.01)
*A61K 39/00* (2006.01)

(52) U.S. Cl.
CPC .......... *C07K 16/2878* (2013.01); *A61K 31/00* (2013.01); *A61K 31/7088* (2013.01); *A61K 31/7105* (2013.01); *A61K 38/2046* (2013.01); *A61K 45/06* (2013.01); *C12N 15/113* (2013.01); *C12N 15/1138* (2013.01); *G01N 33/505* (2013.01); *A61K 2039/505* (2013.01); *C07K 14/5418* (2013.01); *C07K 2317/75* (2013.01); *C12N 2310/14* (2013.01)

(58) Field of Classification Search
CPC ...... A61K 38/00; A61K 39/00; C07K 14/705; C07K 16/28; C07K 14/70596; C07K 14/47; C07K 16/00; C07K 14/00; C12N 5/0636; C12N 5/06; C12N 5/0634
See application file for complete search history.

(56) References Cited

U.S. PATENT DOCUMENTS

| | | | |
|---|---|---|---|
| 8,188,232 B1 | 5/2012 | Murphy | |
| 8,389,739 B1 | 3/2013 | Thacher et al. | |
| 8,658,612 B2 | 2/2014 | Kumon et al. | |
| 2007/0154487 A1* | 7/2007 | Littman | A61K 39/0011 424/185.1 |
| 2008/0248025 A1* | 10/2008 | Roark | C07K 16/18 424/130.1 |
| 2010/0254940 A1 | 10/2010 | Romagne et al. | |
| 2011/0189237 A1 | 8/2011 | Kumon et al. | |

FOREIGN PATENT DOCUMENTS

| | | |
|---|---|---|
| JP | H11508605 A | 7/1999 |
| JP | 2008505080 A | 2/2008 |
| JP | 2013500715 A | 1/2013 |
| WO | WO-2007010692 A1 | 1/2007 |
| WO | WO 2009/037723 A1 | 3/2009 |
| WO | WO 2011/014438 A1 | 2/2011 |
| WO | WO-2013036912 A2 | 3/2013 |
| WO | WO-2015035063 A2 | 3/2015 |

OTHER PUBLICATIONS

Krieg et al. B and T lymphocyte attenuator regulates CD8+ T cell-intrinsic homeostasis and memory cell generation. Nature Immunol 8(2): 162-171, 2007.*
Murphy et al. Balancing co-stimulation and inhibition with BTLA and HVEM. Nature Rev Immunol 6: 671-681, 2006.*
Murphy et al. Slow down and survive: enigmatic immunoregulation by BTLA and HVEM. Ann Rev Immunol 28: 389-411, 2010.*
Otsuki et al. Expression and function of the B and T lymphocyte attenuator (BTLA/CD272) on human T cells. Biochem Biophys Res Comm 344: 1121-1127, 2006.*
Paul et al. Role of gamma-delta T cells in autoimmunity. J Leukoc Biol 97: 259-271, 2015.*
Watanabe et al. BTLA is a lymphocyte inhibitory receptor with similarities to CTLA-4 and PD-1. Nat Immunol 4(7): 670-679, 2003.*
Burgler et al. RORC2 is involved in T cell polarization through interaction with the FOXP3 promoter. J Immunol 184: 6161-6169, 2010.*

(Continued)

*Primary Examiner* — Bridget E Bunner
(74) *Attorney, Agent, or Firm* — Wilson Sonsini Goodrich & Rosati

(57) ABSTRACT

The present invention relate to the discovery that BTLA, IL-7 and RORγt modulate the activity and expression of γδT cells. Specifically, the present invention provides methods of modulating γδT cell homeostasis and function by regulating expression of BTLA. The present invention further provides agents which modulate the activity and expression of BTLA, RORyt and IL-7 and methods for screening of such agents. The present invention also provides methods for treating autoimmune or inflammatory diseases using modulators of BTLA, RORyt and IL-7.

16 Claims, 27 Drawing Sheets

Specification includes a Sequence Listing.

(56) References Cited

OTHER PUBLICATIONS

Hakemi et al. RORC2 gene silencing in human Th17 cells by siRNA: design and evaluation of hightly efficient siRNA. Avicenna J Med Biotech 5(1): 10-19, 2013.*

Chang et al. The therapeutic potential of RORgamma modulators in the treatment of human disease. J Exp Pharmacol 4: 141-148, 2012.*

Huh et al. Small molecule inhibitors of RORgammat: targeting Th17 cells and other applications. Eur J Immunol 42: 2232-2237, 2012.*

Ramstead et al. Complex role of gammadelta T-cell-derived cytokines and growth factors in cancer. J Interferon Cytokine Res 32(12): 563-569, 2012.*

Truong et al. BTLA targeting modulates lymphocyte phenotype, function, and numbers and attenuates disase in nonobese diabetic mice. J Leukocyte Biol 86: 41-51, 2009.*

Vantourout et al. Six-of-the-best: unique contributions of gammadelta T cells to immunology. Nature Rev Immunol 13: 88-100, 2013.*

Watanabe et al. Coinhibitory molecules in autoimmune diseases. Clin Dev Immunol 2012: 269756, 2012.*

Bekiaris, Vasileios et al.: "*The Inhibitory Receptor BTLA Controls [gamma][delta] T Cell Homeostasis and Inflammatory Responses*"; Immunity., vol. 39, No. 6, Dec. 5, 2013, 31 pages, XP055361147.

Gertner-Dardenne, J. et al.: "*The co-receptor BTLA negatively regulates human V 9V 2 T-cell proliferation: a potential way of immune escape for lymphoma cells*"; Blood, vol. 122, No. 6, Aug. 8, 2013, pp. 922-931.

Oki, Mie et al.: "*A Functional Polymorphism in B and T Lymphocyte Attenuator Is Associated with Susceptibility to Rheumatoid Arthritis*"; Clinical & Developmental Immunology, vol. 2011, Jan. 1, 2011, pp. 1-8.

Partial European Search Report dated May 18, 2017, regarding EP 14 84 2359.

Wakita, Daiko et al.: "*Tumor-infiltrating IL-17-producing [gamma][delta] T cells support the progression of tumor by promoting angiogenesis*"; European Journal of Immunology, vol. 40, No. 7, Jul. 15, 2010, pp. 1927-1937.

PCT/US2014/054116 International Search Report and Written Opinion dated Jan. 21, 2015.

* cited by examiner

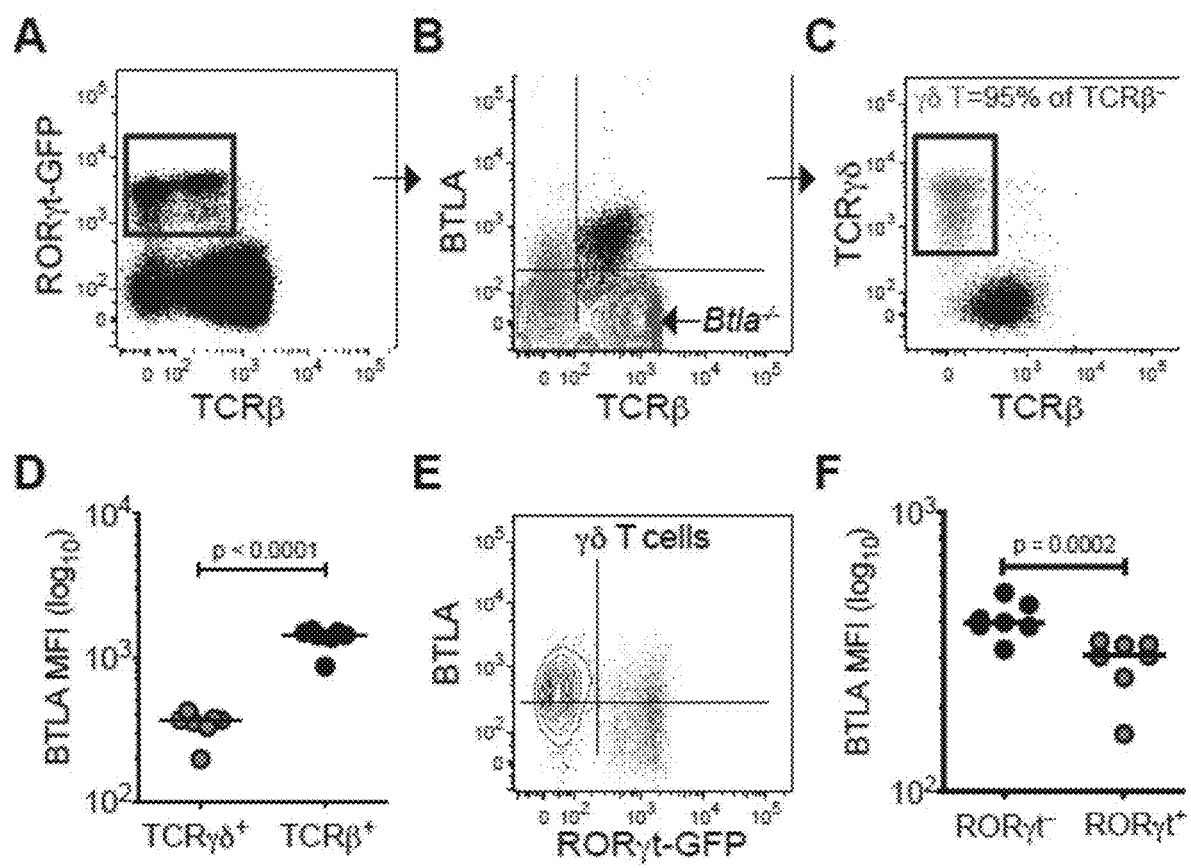
FIG. 1A-F

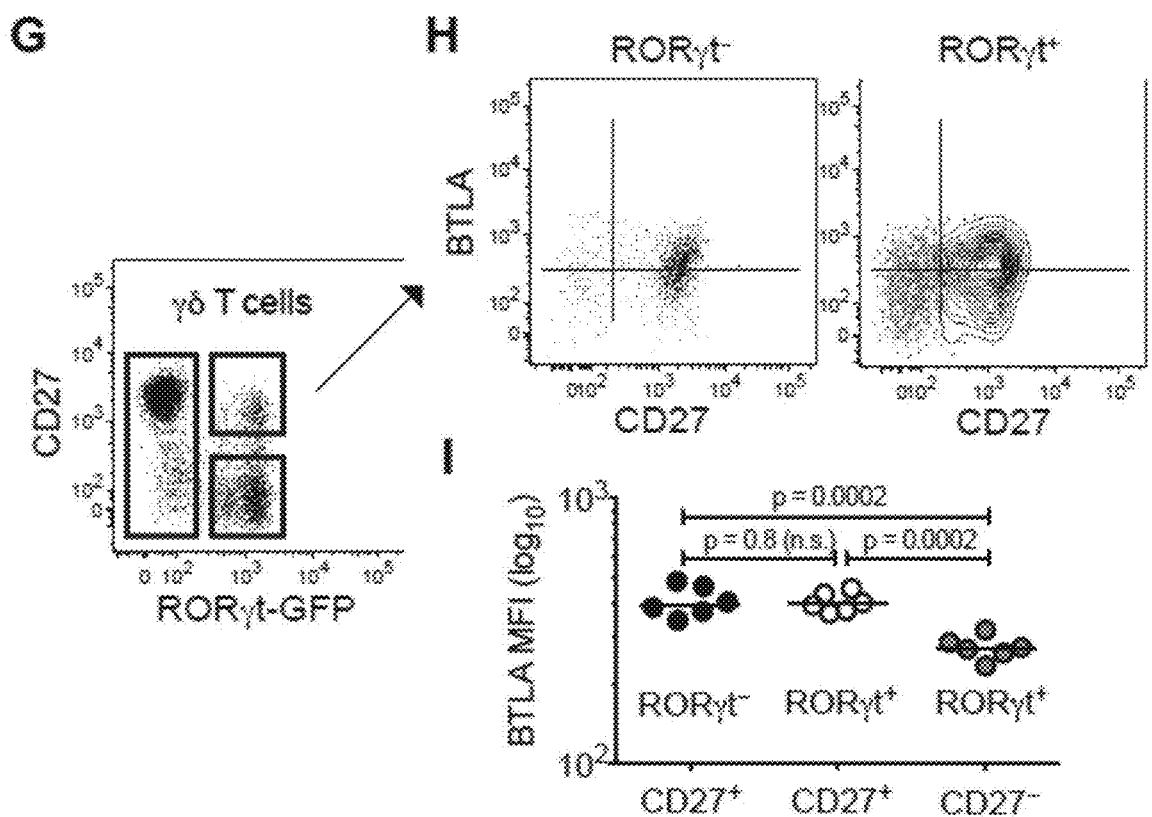
FIG. 1G-I

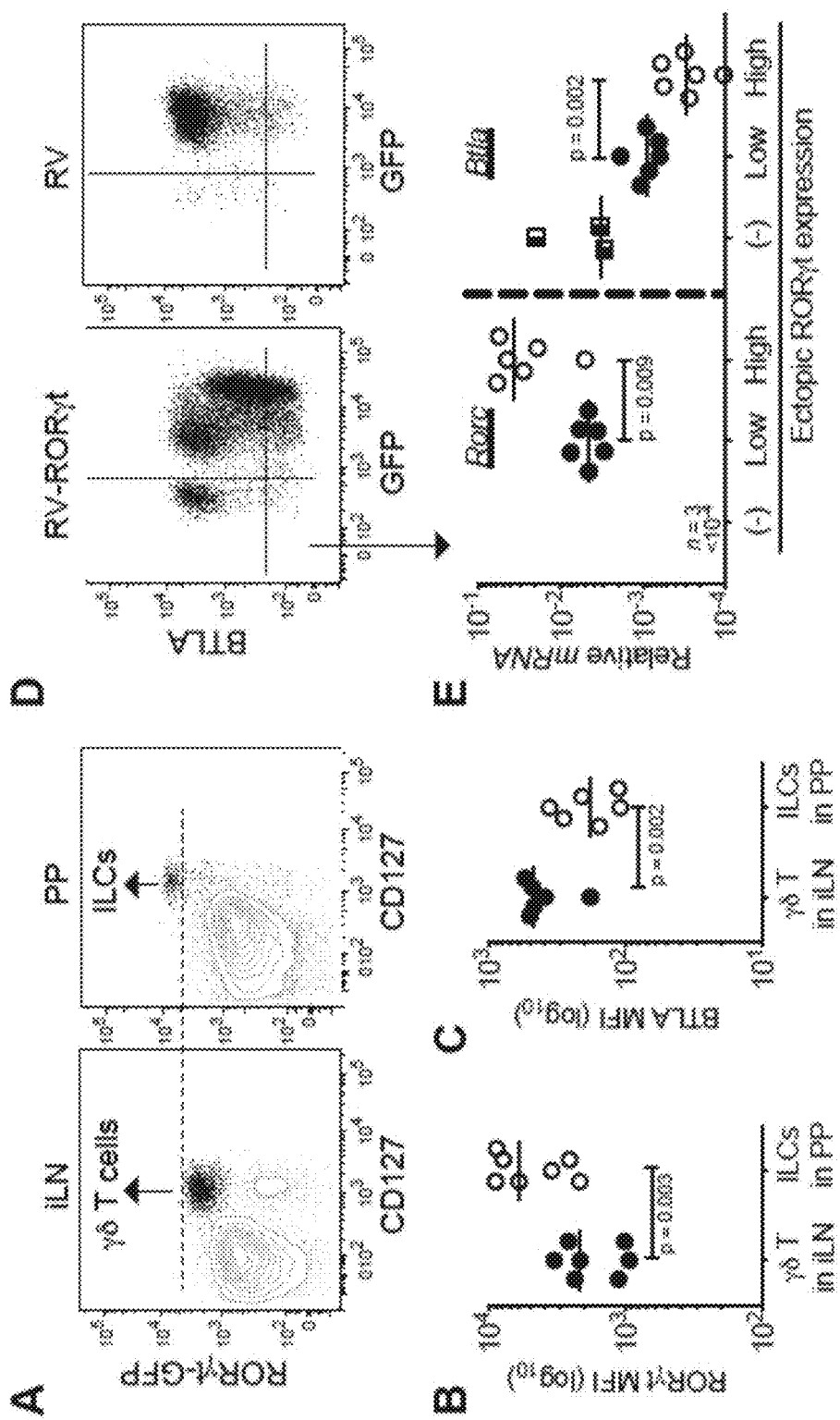
FIG. 2A-E

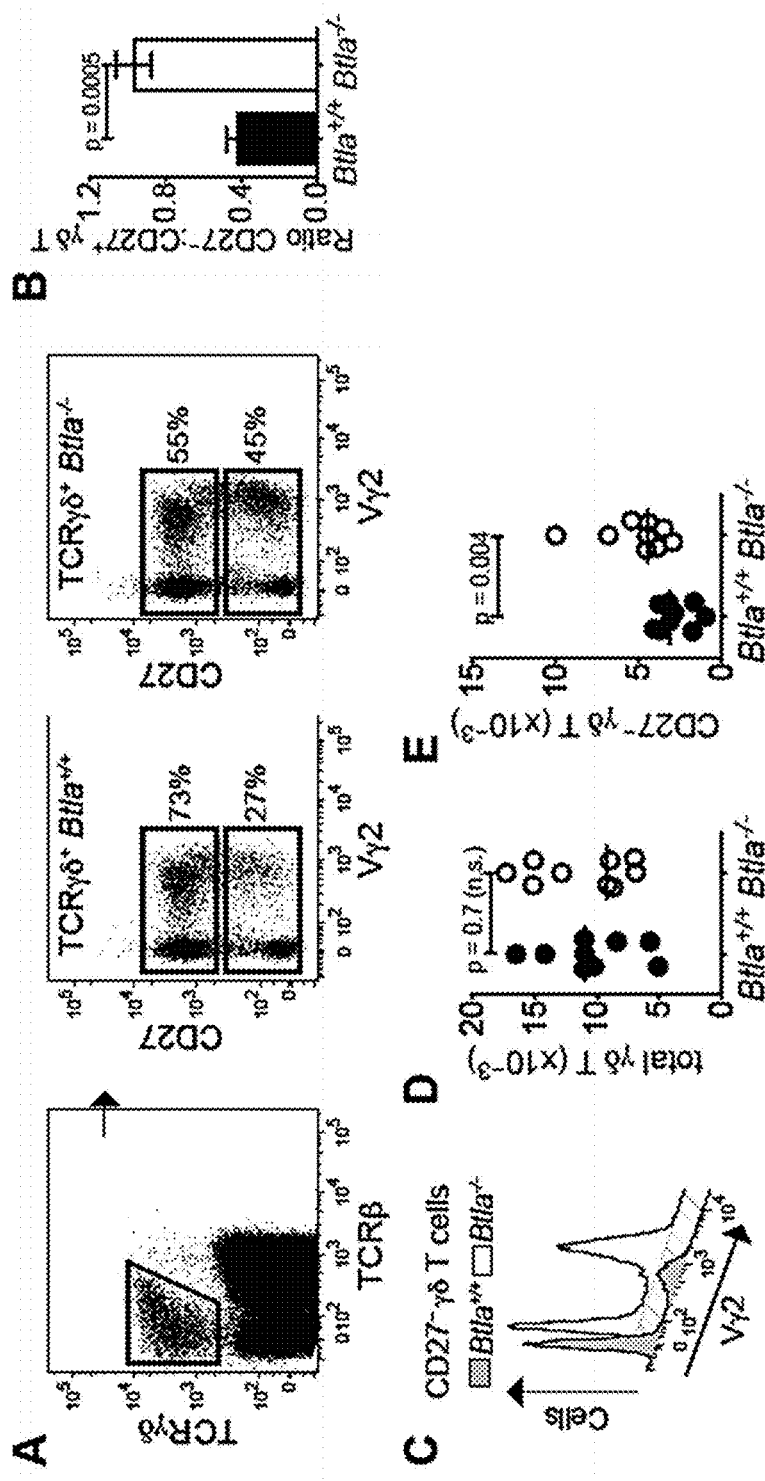
FIG. 3A-E

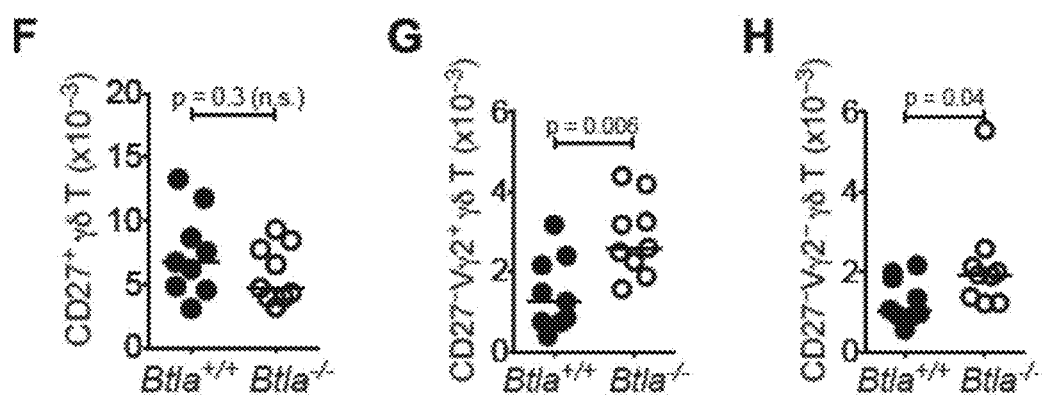
FIG. 3F-H

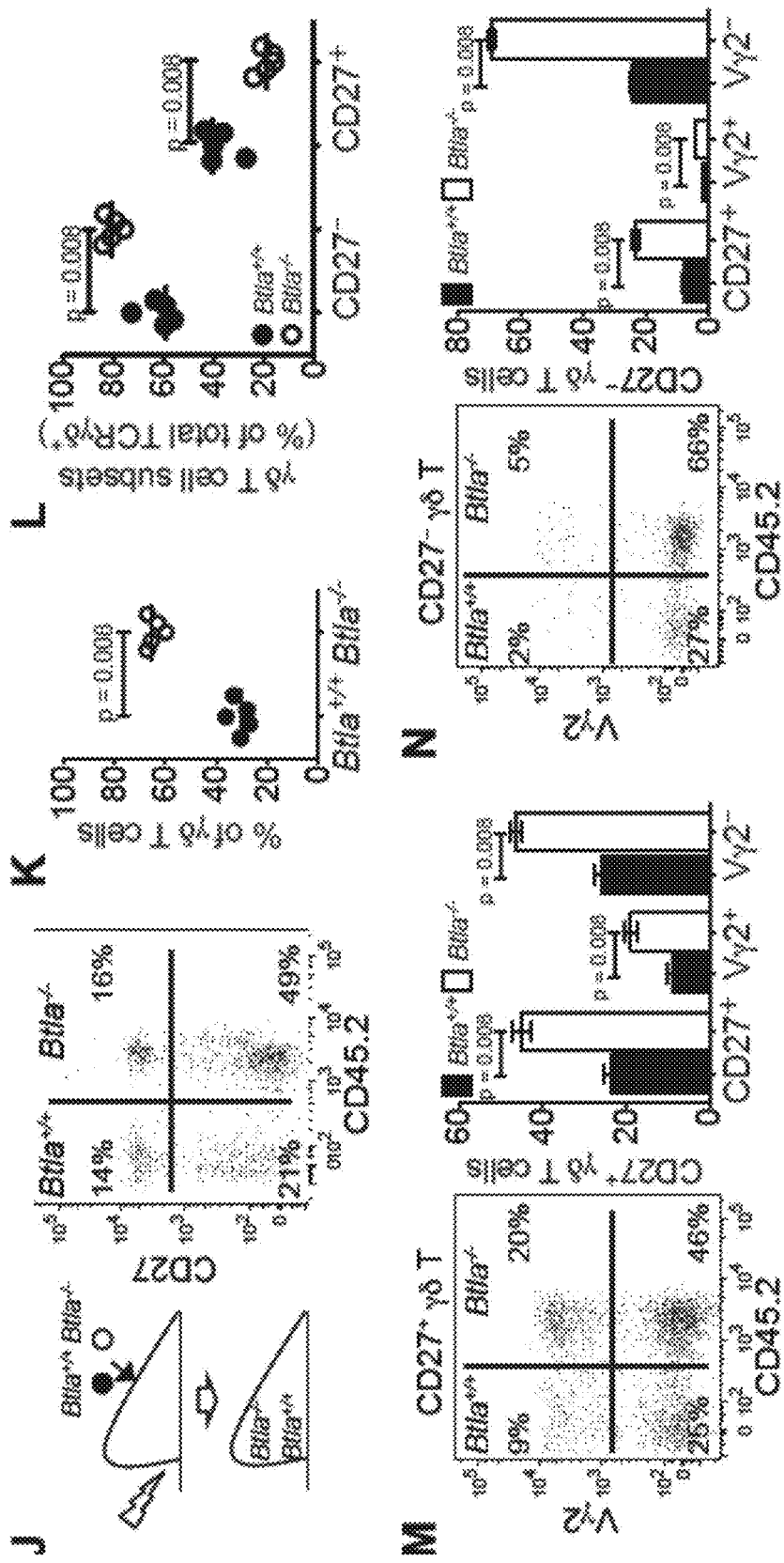
FIG. 3J-N

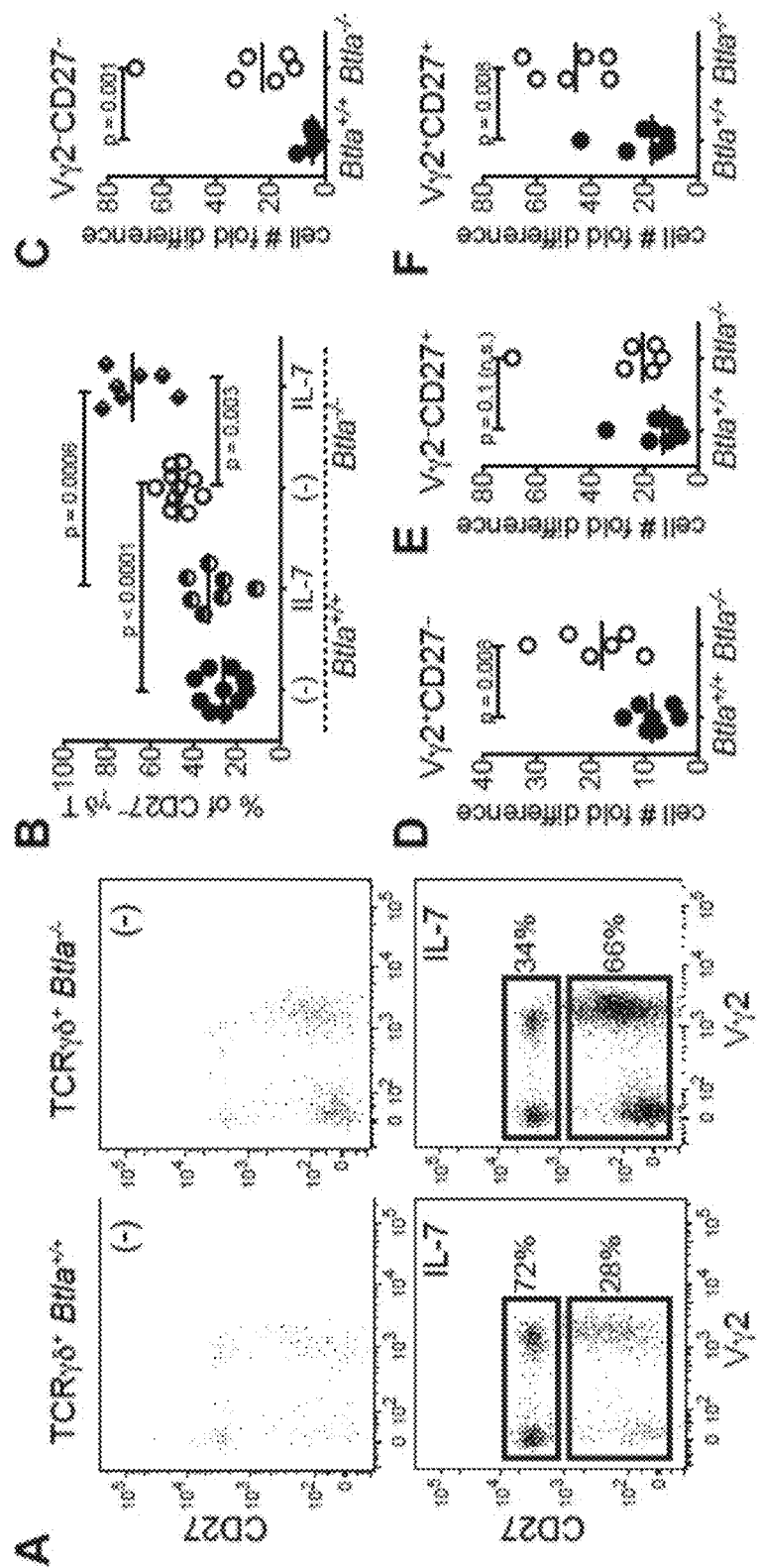
FIG. 4A-F

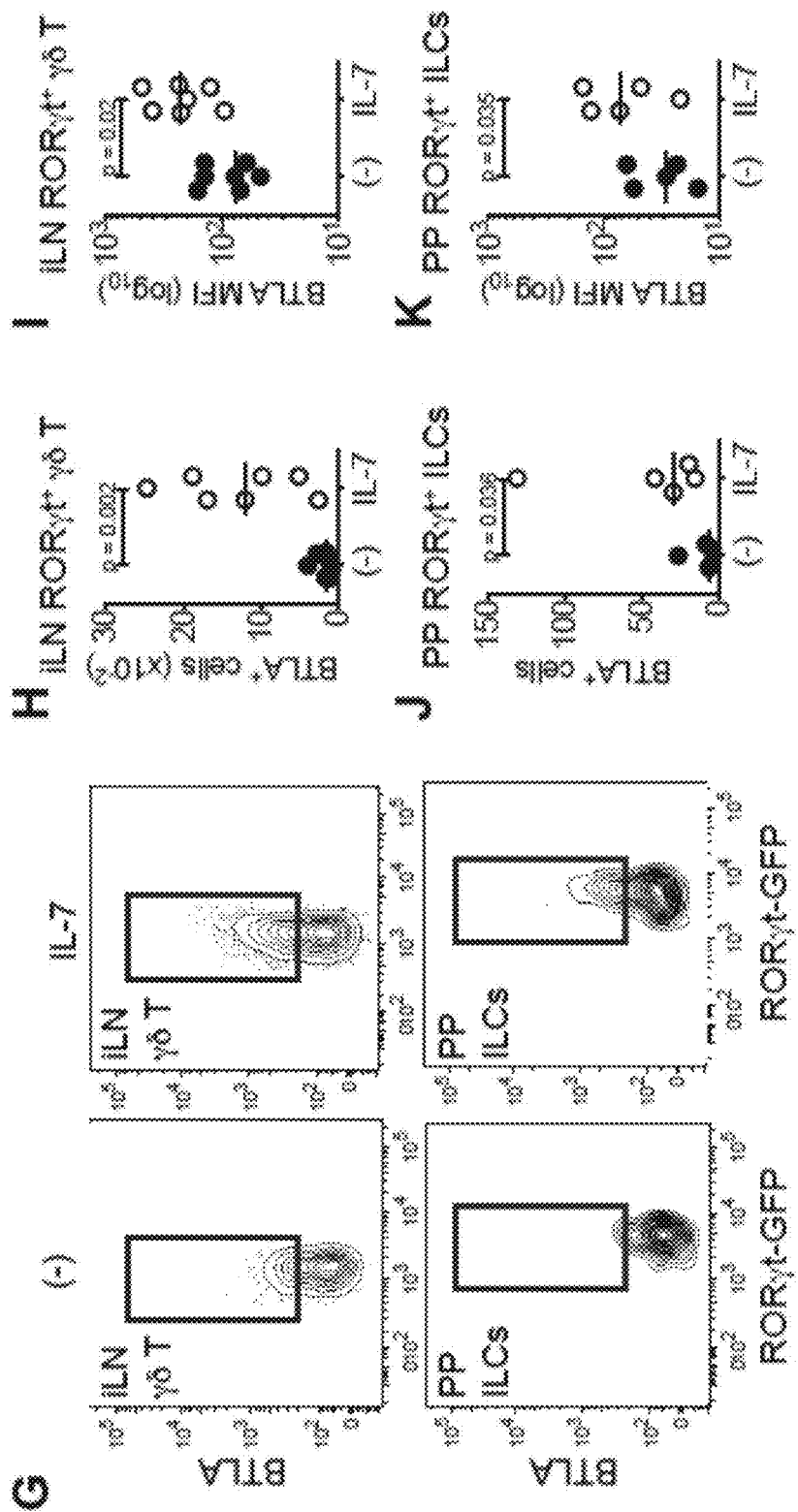
FIG. 4G-K

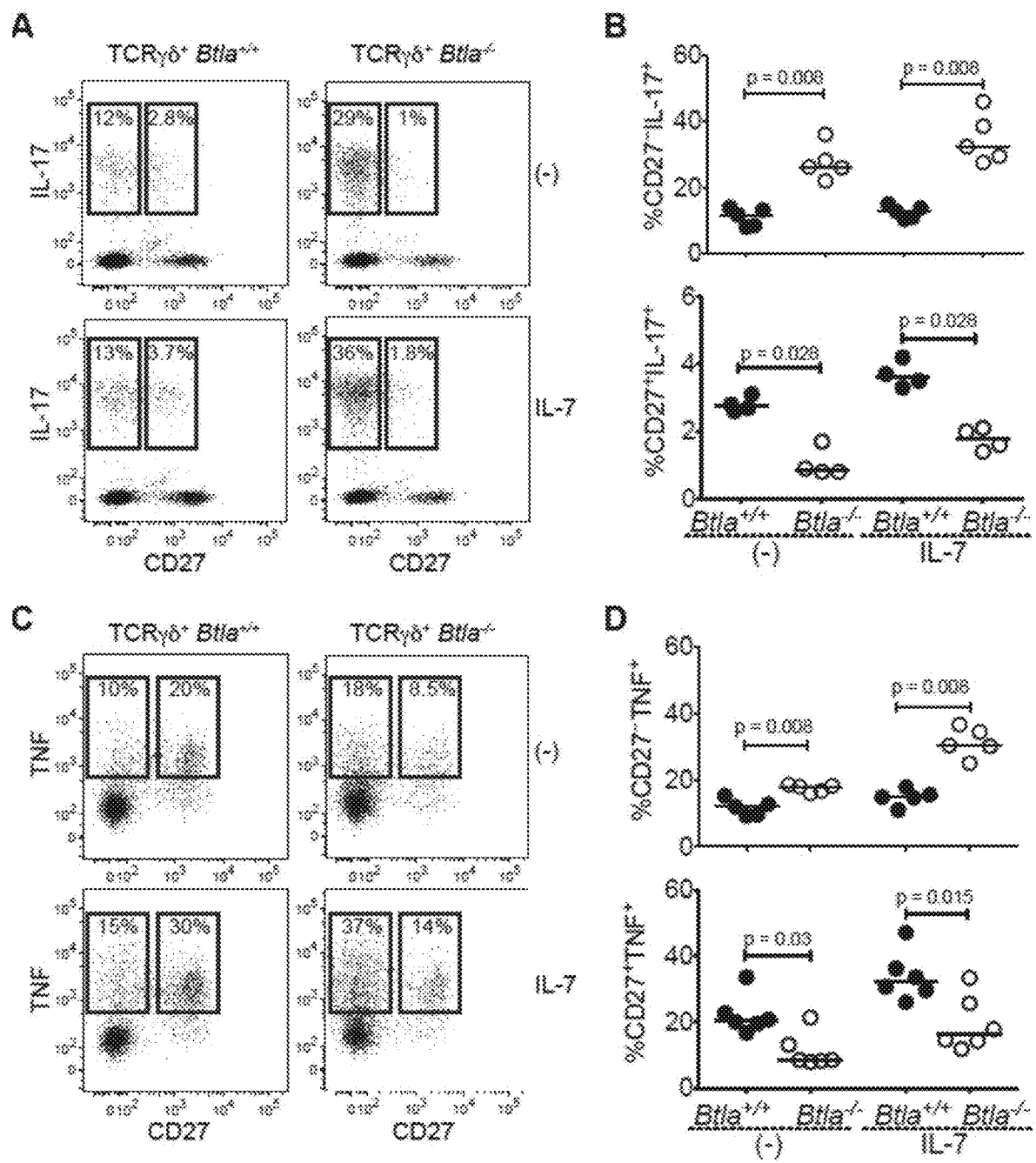
FIG. 5A-D

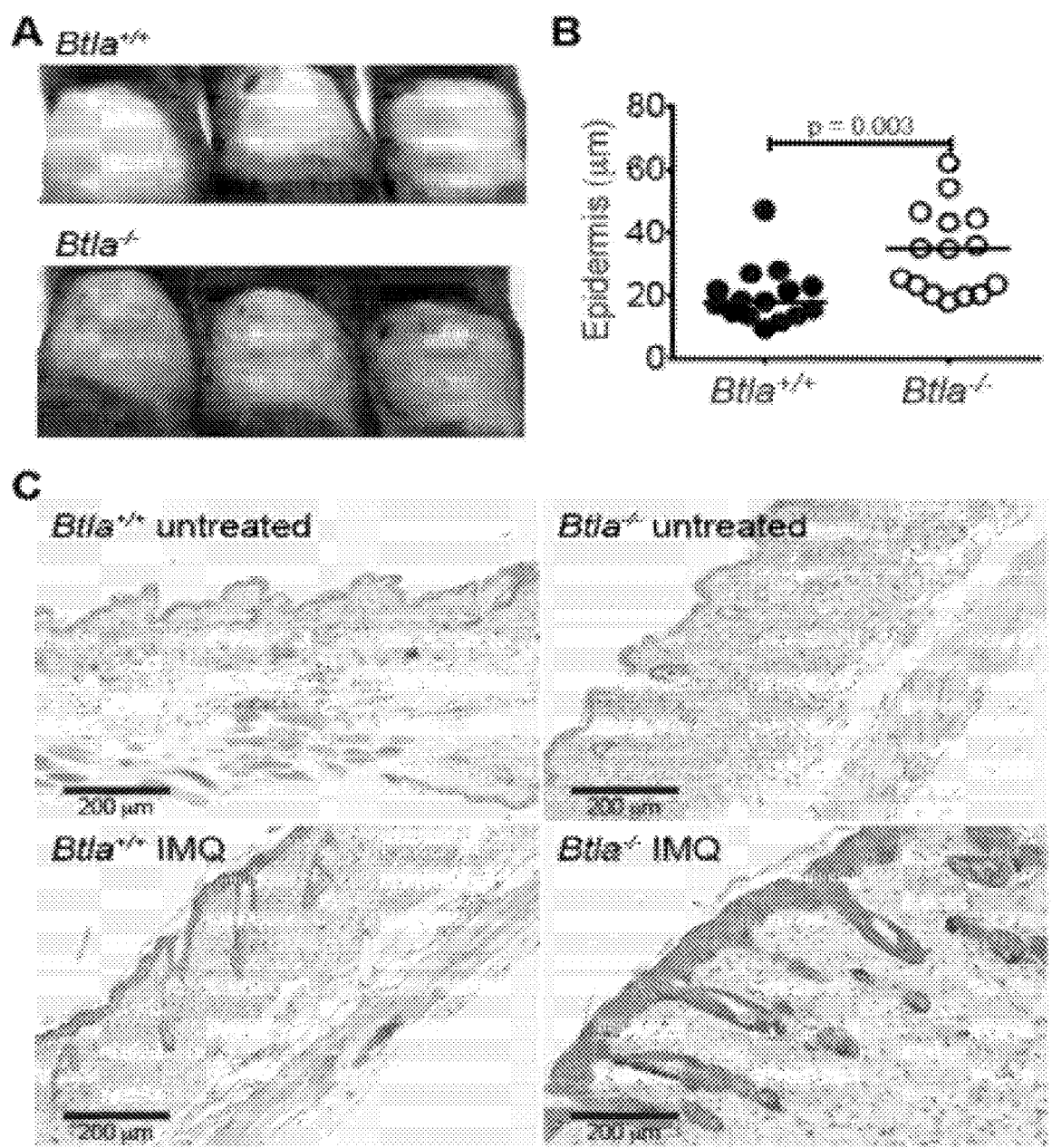
FIG. 6A-C

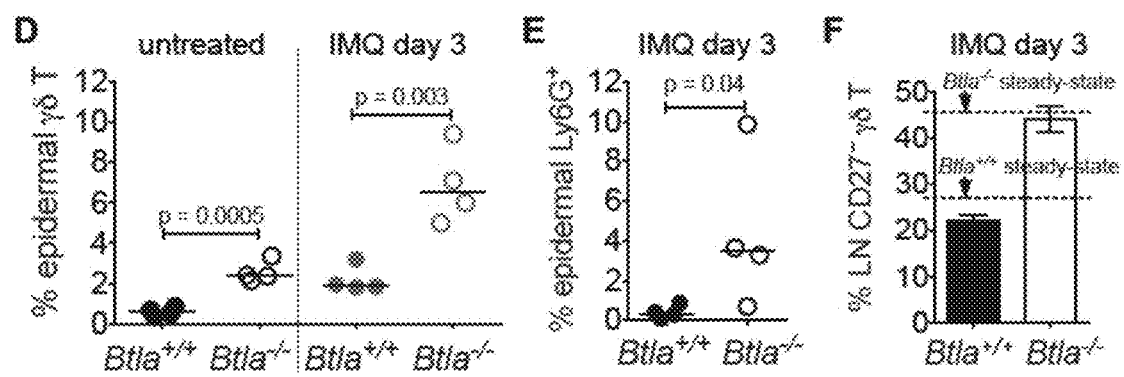
FIG. 6D-F
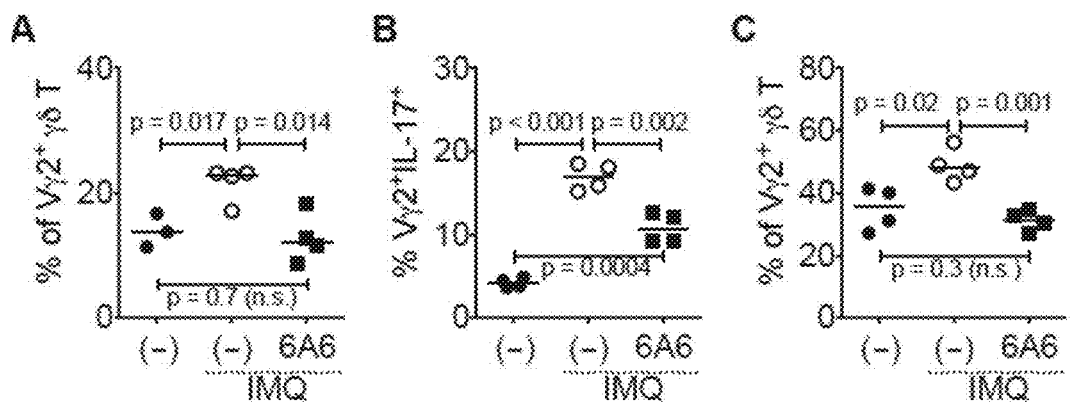
FIG. 7A-C

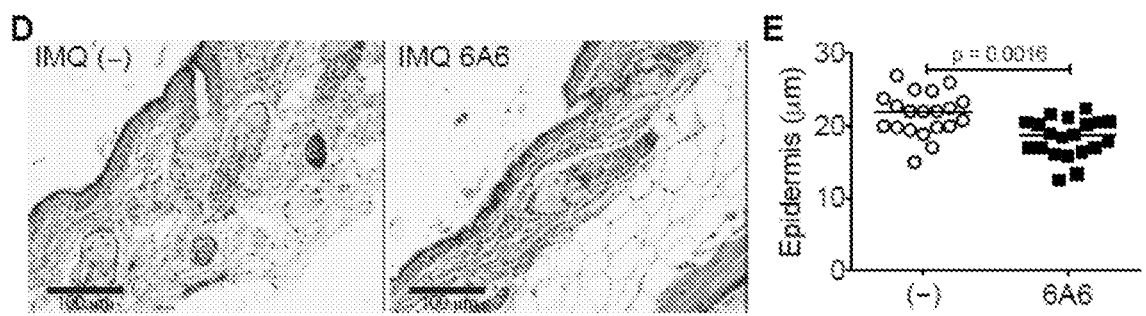
FIG. 7D-E

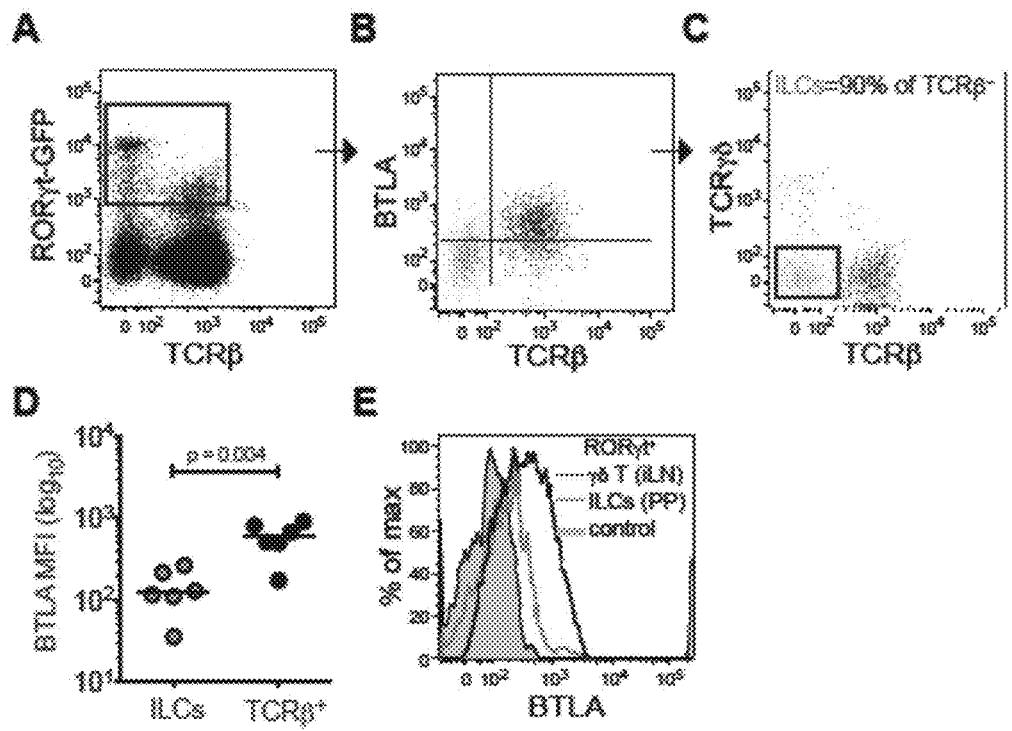
FIG. 8A-E
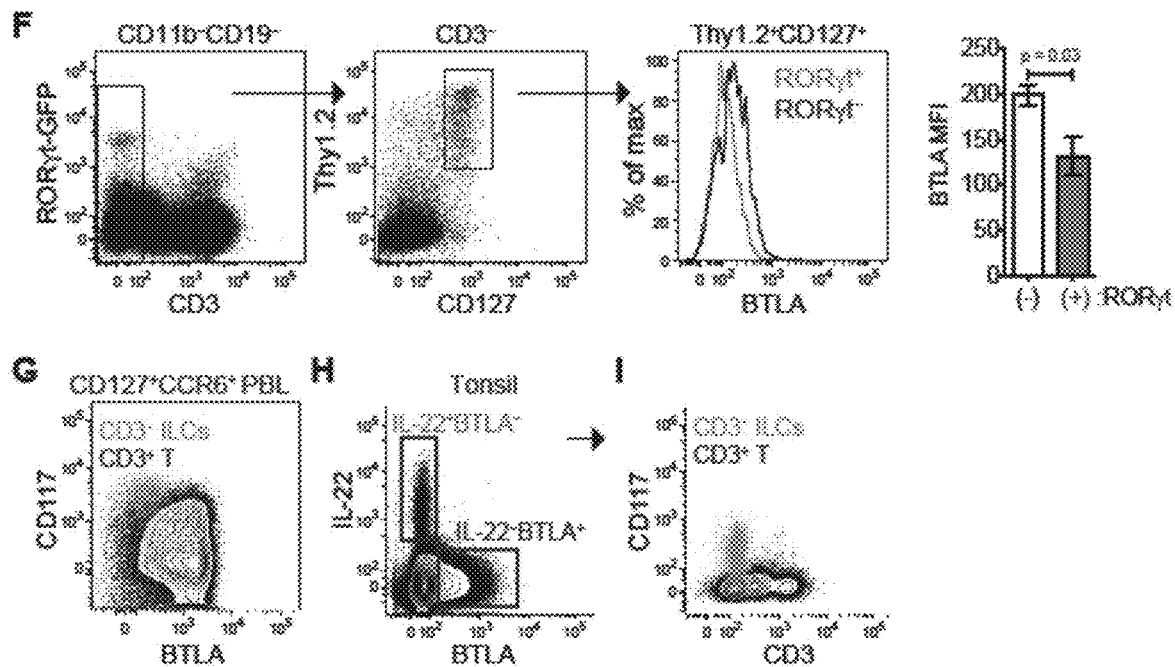
FIG. 8F-I

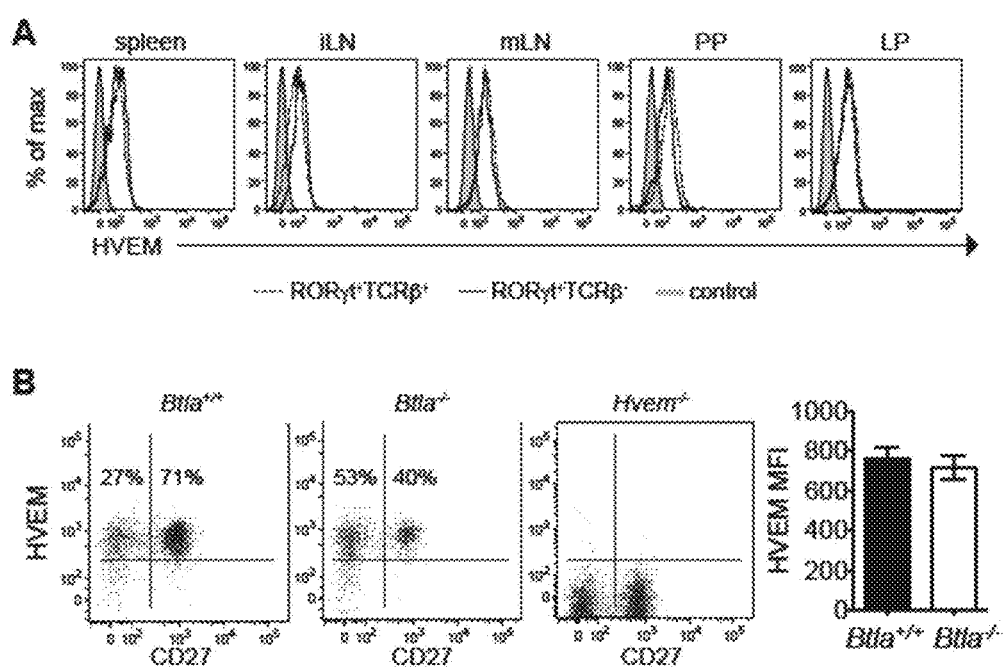
FIG. 9A-B

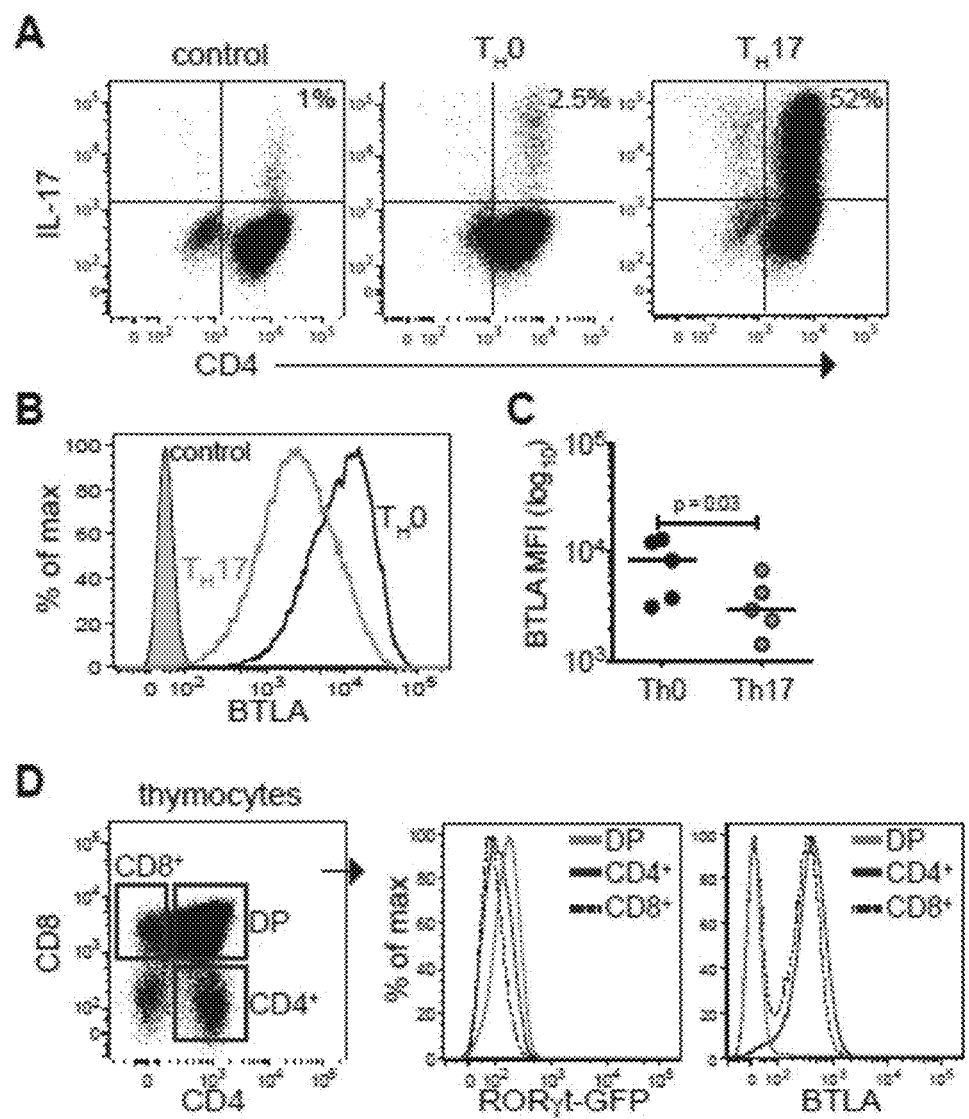
FIG. 10A-D

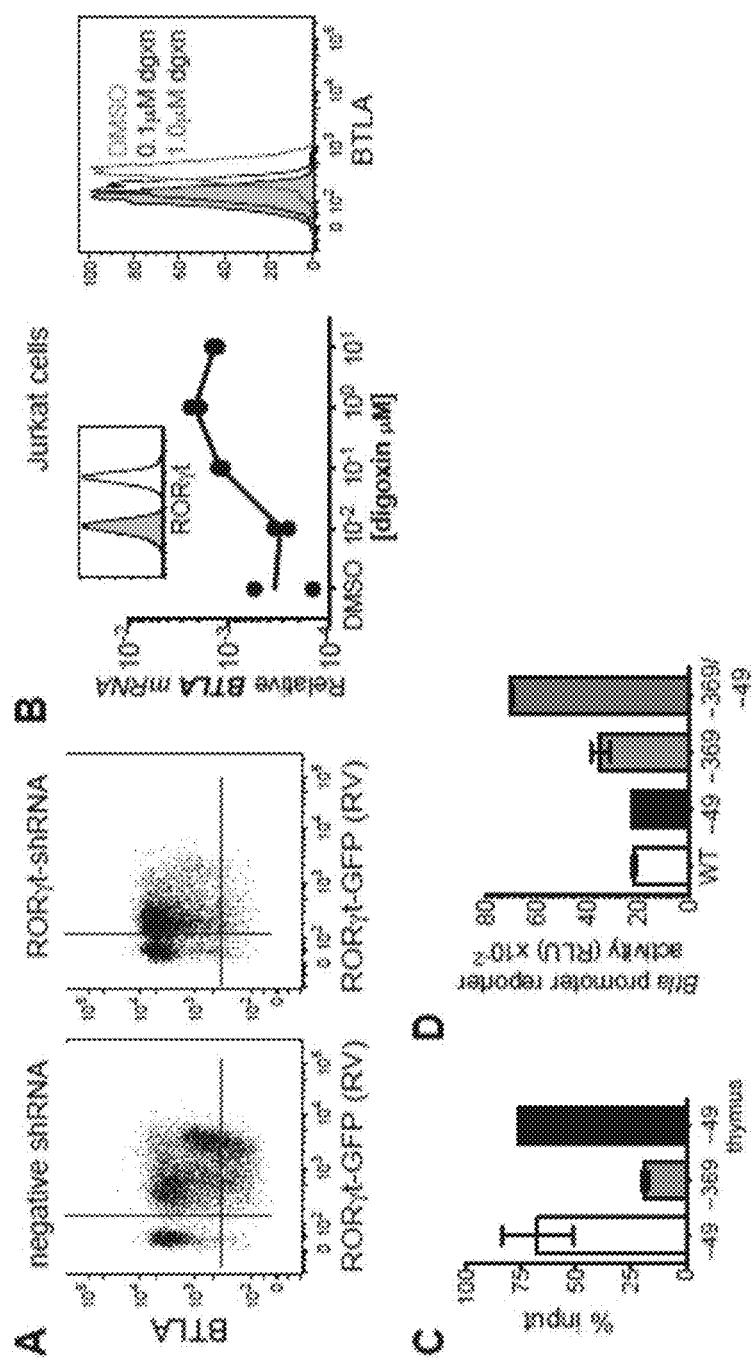
FIG. 11A-D

FIG. 13A-B

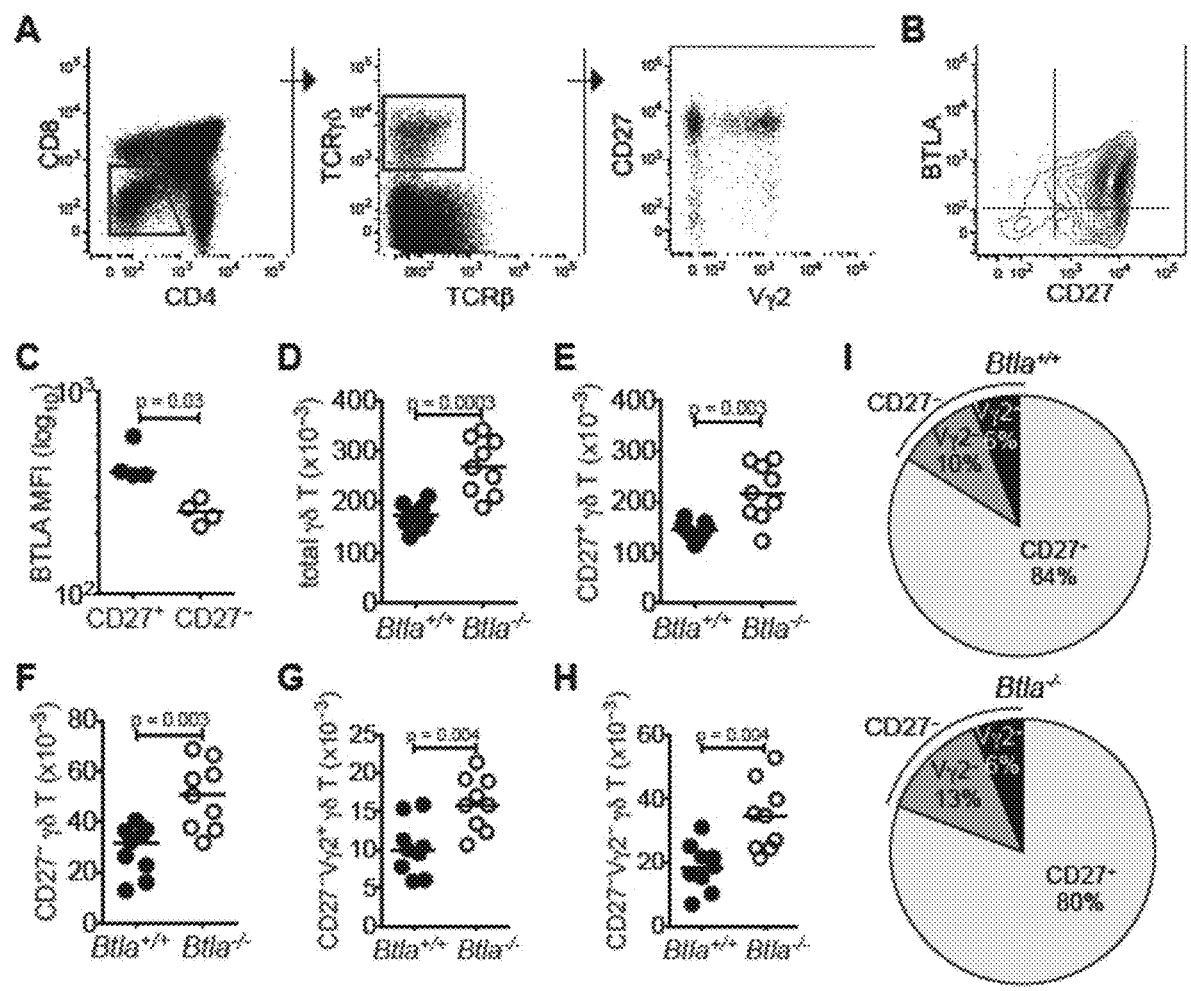
FIG. 14A-I

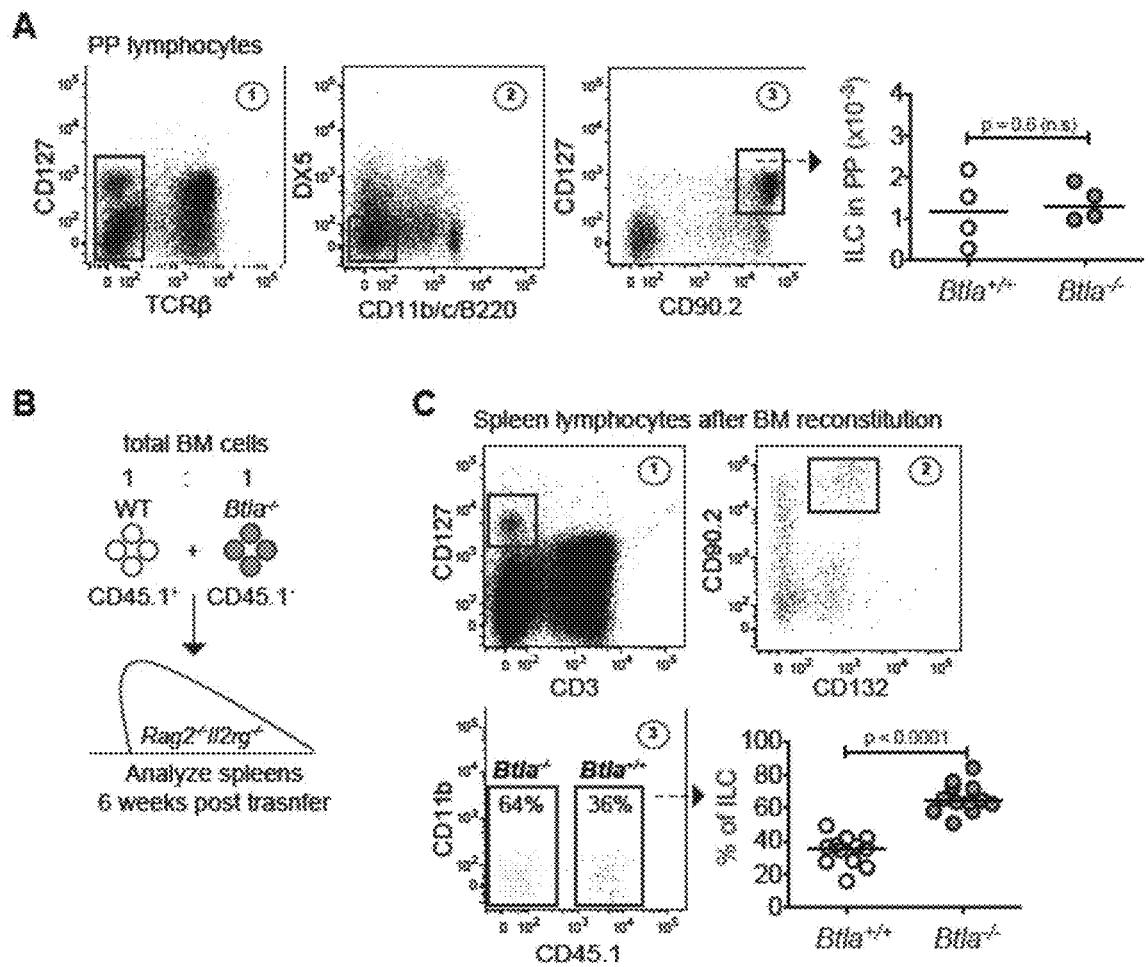
FIG. 15A-C
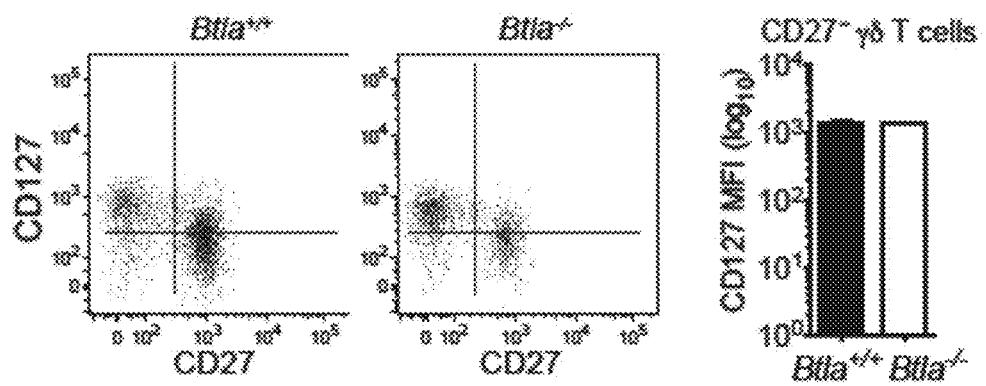
FIG. 16

FIG. 17A-B

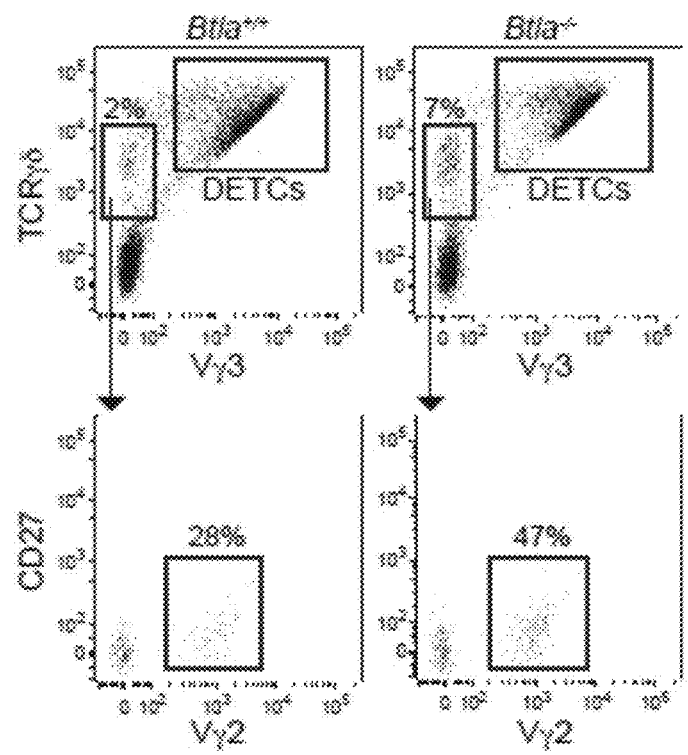
FIG 19
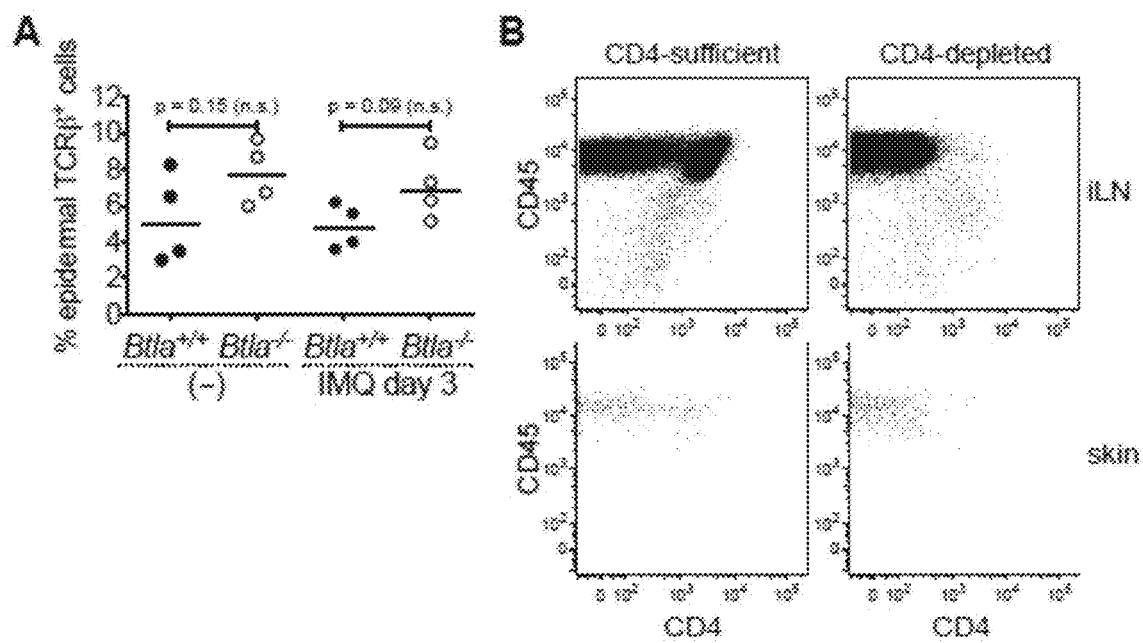
FIG. 20A-B

SEQUENCE LISTING

```
<160> NUMBER OF SEQ ID NOS: 23

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
acctcttttc acgggagga                                                      19

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
tcccacatct cccacattg                                                      19

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
gggaattctt catcctccat c                                                   21

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gttgcactgg acactcttca tc                                                  22

<210> SEQ ID NO 5
<211> LENGTH: 20
<212> TYPE: DNA
<213> ORGANISM: Artificial Sequence
<220> FEATURE:
<223> OTHER INFORMATION: Primer
```

```
<400> SEQUENCE: 5
caccaggtct cctgatttga                                               20

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
aggagtccca agcatggca                                                19

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
ggttgtaaga tacattacac tg                                            22

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
tctaaattgt tacagtcttt agg                                           23

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
agtcggatcc tgcatgcagt gtatcaggaa tag                                33

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
agtcaagctt tcccagcacg tgtcaggtaa g                                  31

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
gccttcccta gcactgatgt tgaatcccc                                     29

<210> SEQ ID NO 12
```

```
<211> LENGTH: 28
<212> TYPE: DNA
<213> ORGANISM: Artificial Sequence
<220> FEATURE:
<223> OTHER INFORMATION: Primer

<400> SEQUENCE: 12
catcagtgct agggaaggcg gcttggac                                          28

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
cacctgtgag gaaacaactg caacagcagc                                        30

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
cagttgtttc ctcacaggtg ataaccccg                                         29

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
tgtgaataac gtcacggagc tctgaagatc tctaggg                                37

<210> SEQ ID NO 16
<211> LENGTH: 38
<212> TYPE: DNA
<213> ORGANISM: Artificial Sequence
<220> FEATURE:
<223> OTHER INFORMATION: Primer

<400> SEQUENCE: 16
cttcagagct ccgtgacgtt attcacacta gcagcatc                               38

<210> SEQ ID NO 17
<211> LENGTH: 44
<212> TYPE: DNA
<213> ORGANISM: Artificial Sequence
<220> FEATURE:
<223> OTHER INFORMATION: Primer

<400> SEQUENCE: 17
tatgaatttc ctcacggtga tttgatcaga atctaaacct aaag                        44

<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
```
ctgatcaaat caccgtgagg aaattcatac aaaaagtacc                          40

<210> SEQ ID NO 19
<211> LENGTH: 223
<212> TYPE: DNA
<213> ORGANISM: Artificial Sequence
<220> FEATURE:
<223> OTHER INFORMATION: Primer

<400> SEQUENCE: 19 aaagggaaa tatatgctta ccataggtac tttttgtatg aatttcctga ccctgatttg     60
atcagaatct aaacctaaag actgtaacaa tttagatctt ttttttttta agtttaattg    120 ttcacttta agatgctgct agtgtgaata acgtgaccca gctctgaaga tctctaggga    180
ggaagaggaa gtttgccctt acctgacacg tgctgggaat gaa                     223

<210> SEQ ID NO 20
<211> LENGTH: 236
<212> TYPE: DNA
<213> ORGANISM: Homo sapiens

<400> SEQUENCE: 20
caaaggggaa aatgtatact taccattgat agttttacca taaatttcct gaccttaatt   60
tgattaaaat ctcaacttaa agactgcaac aatacagatt tctttaaagt ttaattgctc   120
atttcacaga tgccactggg gtaggtaaac tgacccaact ctgcagcact cagaagacga   180
agcaaagcct tctacttgag cagttttttcc atcactgata tgtgcaggaa atgaag     236

<210> SEQ ID NO 21
<211> LENGTH: 494
<212> TYPE: PRT
<213> ORGANISM: Mus musculus

<400> SEQUENCE: 21

Met Arg Thr Gln Ile Glu Val Ile Pro Cys Lys Ile Cys Gly Asp Lys
1               5                   10                  15

Ser Ser Gly Ile His Tyr Gly Val Ile Thr Cys Glu Gly Cys Lys Gly
            20                  25                  30

Phe Phe Arg Arg Ser Gln Gln Cys Asn Val Ala Tyr Ser Cys Thr Arg
        35                  40                  45

Gln Gln Asn Cys Pro Ile Asp Arg Thr Ser Arg Asn Arg Cys Gln His
    50                  55                  60

Cys Arg Leu Gln Lys Leu Cys Ala Leu Gly Met Ser Arg Asp Ala Val
65                  70                  75                  80

Lys Gly Arg Met Ser Lys Lys Gln Arg Asp Ser Leu His Ala Glu Val
                85                  90                  95

Gln Lys Gln Leu Gln Gln Gln Gln Gln Glu Gln Val Ala Lys Thr
            100                 105                 110

Pro Pro Ala Gly Ser Arg Gly Ala Asp Thr Leu Thr Tyr Leu Gly Leu
        115                 120                 125

Ser Asp Gly Gln Leu Pro Leu Gly Ala Ser Pro Asp Leu Pro Glu Ala
    130                 135                 140

```
Ser Ala Cys Pro Pro Gly Leu Leu Arg Ala Ser Gly Ser Gly Pro Pro
145                 150                 155                 160

Tyr Ser Asn Thr Leu Ala Lys Thr Glu Val Gln Gly Ala Ser Cys His
            165                 170                 175

Leu Glu Tyr Ser Pro Glu Arg Gly Lys Ala Glu Gly Arg Asp Ser Ile
        180                 185                 190

Tyr Ser Thr Asp Gly Gln Leu Thr Leu Gly Arg Gly Leu Arg Phe Glu
    195                 200                 205

Glu Thr Arg His Pro Glu Leu Gly Glu Pro Glu Gln Gly Pro Asp Ser
        210                 215                 220

His Cys Ile Pro Ser Phe Cys Ser Ala Pro Glu Val Pro Tyr Ala Ser
225                 230                 235                 240

Leu Thr Asp Ile Glu Tyr Leu Val Gln Asn Val Cys Lys Ser Phe Arg
                245                 250                 255

Glu Thr Cys Gln Leu Arg Leu Glu Asp Leu Leu Arg Gln Arg Thr Asn
            260                 265                 270

Leu Phe Ser Arg Glu Glu Val Thr Ser Tyr Gln Arg Lys Ser Met Trp
        275                 280                 285

Glu Met Trp Glu Arg Cys Ala His Asn His Leu Thr Glu Ala Ile Gln
290                 295                 300

Tyr Val Val Glu Phe Ala Lys Arg Leu Ser Gly Phe Met Glu Leu Cys
305                 310                 315                 320

Gln Asn Asp Gln Ile Ile Leu Leu Lys Ala Gly Ala Met Glu Val Val
                325                 330                 335

Leu Val Arg Met Cys Arg Ala Tyr Asn Ala Asn Asn His Thr Phe Phe
            340                 345                 350

Glu Gly Lys Tyr Gly Gly Val Glu Leu Phe Arg Ala Leu Gly Cys Ser
        355                 360                 365

Glu Leu Ile Ser Ser Ile Phe Asp Phe Ser His Phe Leu Ser Ala Leu
    370                 375                 380

Cys Phe Ser Glu Asp Glu Ile Ala Leu Tyr Tyr Thr Ala Leu Val Leu
385                 390                 395                 400

Val Ile Asn Asn Ala Arg Pro Gly Leu Gln Glu Lys Arg Arg Val Glu
                405                 410                 415

His Leu Gln Tyr Asn Leu Glu Leu Ala Phe His His Leu Cys Lys
            420                 425                 430

Thr His Arg Gln Gly Leu Leu Ala Lys Leu Pro Pro Lys Gly Lys Leu
        435                 440                 445

Arg Ser Leu Cys Gln His Val Glu Lys Leu Gln Ile Phe His Gln His
450                 455                 460

Leu His Pro Ile Val Val Gln Ala Ala Phe Pro Pro Leu Tyr Lys Glu
465                 470                 475                 480

Leu Phe Ser Thr Asp Val Glu Ser Pro Glu Gly Leu Ser Lys
                485                 490
```

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
ctgccagaat gaccagatt                                              19

```
<210> SEQ ID NO 23
<211> LENGTH: 9
<212> TYPE: DNA
<213> ORGANISM: Artificial Sequence
<220> FEATURE:
<223> OTHER INFORMATION: Synthetic

<400> SEQUENCE: 23 ttcaagaga                                                                          9
```

MODULATION OF γδ T CELLS

CROSS REFERENCE TO RELATED APPLICATIONS

This application is a 35 U.S.C. § 371 National Stage application of International Application No. PCT/US2014/054116 filed Sep. 4, 2014, now pending; which claims the benefit under 35 U.S.C. § 119(e) to U.S. Application Ser. No. 61/874,269 filed Sep. 5, 2013. The disclosure of each of the prior applications is considered part of and is incorporated by reference in the disclosure of this application.

STATEMENT AS TO FEDERALLY SPONSORED RESEARCH

This invention was made with government support under R37 AI033068, R01 CA164679, R01 AI048073, and R01 AI067890 awarded by the National Institutes of Health. The government has certain rights in the invention.

FIELD OF THE INVENTION

The invention pertains to the field of T cell mediated immune response. Specifically, the invention relates to the modulation of the level and activity of γδT cells by RORγt, IL-7 and BTLA.

INCORPORATION OF SEQUENCE LISTING

The material in the accompanying sequence listing is hereby incorporated by reference into this application. The accompanying sequence listing text file, name BURN1650_1WO_Sequence_Listing, was created on 4 Sep. 2014, and is 9 kb. The file can be assessed using Microsoft Word on a computer that uses Windows OS.

BACKGROUND OF THE INVENTION

The differentiation of specific subsets of T cells is promoted by expression of the transcription factor retinoid-related orphan receptor-γ isoform-t (RORγt) (encoded by Rorc). RORγt is a member of the ROR family of transcription factors that transactivate gene expression by recruiting nuclear repressors or activators containing an LXXLL motif via their activating function-2 (AF2) domain to canonical ROR DNA binding sites through their DNA binding domain (DBD). In T cells, RORγt binds and activates the promoter of the Il17 gene to express the pro-inflammatory cytokine IL-17, driving the differentiation of conventional $CD4^+$ $T_H$ cells (TH17) and sustaining innate-like gamma-delta (γδ) T cells. Phenotypic profiling of γδT cells identified two broad subgroups based on the expression of CD27, a member of the tumor necrosis factor receptor superfamily (TNFRSF). Thus, the $CD27^+$ subset produces IFNγ whereas the $CD27^-$ subset produces IL-17. During development γδT cells are largely dependent on IL-7 signaling, which regulates the survival of early thymic progenitors and induces V(D)J recombination in the TCR-γ locus. Moreover, IL-7 maintains the homeostasis of γδT cells and preferentially expands the $CD27^-IL-17^+$ subset. The capacity of γδT cells to produce IL-17 is acquired during thymic differentiation, independently of TCR signaling, a feature pointing to their bona fide innate nature. γδT cells have emerged as potent inflammatory effectors that can be activated through innate as well as antigen receptors, either of which initiate rapid responses to infection.

RORγt is also essential for the differentiation of group 3 ILCs, such as lymphoid tissue inducer (LTi) cells, which are required for the development of secondary lymphoid organs, and in the adult IL-22 secreting ILCs ($CD134^+IL-22^+$ ILC), which are important for protection against intestinal infections and induce signals for survival of activated lymphocytes. The conservation of the ILC lineage in mice and primates underscores the importance of these cells in the rapid innate defense mechanisms in lymphoid tissues.

The broad expression profile in hematopoietic cells of the inhibitory receptor, B and T lymphocyte attenuator (BTLA) suggested a potential role in regulation of innate-like T cells and ILCs. BTLA belongs to the immunoglobulin superfamily, contains two immunoreceptor tyrosine-based inhibitory motifs (ITIM) and associates with the Src-homology domain 2 (SH2)-containing protein tyrosine phosphatase (SHP)-1 and SHP-2. Through ligation with the herpesvirus entry mediator (HVEM, TNFRSF14) BTLA maintains the homeostasis of dendritic cells and memory T cells, and plays an important role in limiting T cell activation. In contrast to other inhibitory receptors that are induced following activation, BTLA is constitutively expressed in most immune cells. However, the levels of BTLA vary substantially among different lymphoid and myeloid cell types suggesting regulation of BTLA expression may be an important factor in controlling homeostasis in lymphoid tissues.

Herein it is demonstrated that RORγt and IL-7 influence γδT cell homeostasis and function by regulating expression of BTLA. The activating function-2 domain of RORγt is required to repress BTLA transcriptional activity, while IL-7 increases surface levels of BTLA. BTLA limits γδT cell numbers and sustains the normal distribution of γδT subsets by restricting IL-7 responsiveness and expansion of the $CD27^-RORγt^+$ population. Importantly, BTLA regulates IL-17 and TNF production. Consequently, BTLA-deficient animals exhibit enhanced disease in a γδT cell dependent model of dermatitis. Therefore, by coordinating expression of BTLA, RORγt and IL-7 balance suppressive and activation stimuli to regulate γδT cell homeostasis and inflammatory responses.

SUMMARY OF THE INVENTION

The present invention relates to the discovery that BTLA, IL-7 and RORγt modulate the activity and level of γδT cells. Specifically, the present invention provides methods of modulating γδT cell homeostasis and function by regulating expression of BTLA. The present invention further provides agents which modulate the activity and expression of BTLA, RORγt and IL-7 and methods for screening of such agents. The present invention also provides methods for treating autoimmune or inflammatory diseases using modulators of BTLA, RORγt and IL-7.

In one embodiment, the invention provides a method of treating an inflammatory or autoimmune disease in a subject in need thereof comprising administering to the subject one or more agents that modulate the level and/or activity of γδT cells, thereby treating the inflammatory or autoimmune disease. In one aspect, the agent increases B and T lymphocyte attenuator (BTLA) expression or activity. In another aspect, the agent inhibits retinoid-related orphan receptor gamma-isoform-t (RORγt) expression or activity. In an aspect, the agent increases IL-7 expression or activity. In one aspect, the agent modulates the production of IL-17 or TNF by γδT cells. In an aspect, the agent modulates the levels of $RORγt^-$ γδT cells or $RORγt^+$ γδT cells. In another aspect, one agent increases BTLA expression or activity and a second agent inhibits RORγt expression or activity. In a further aspect, the agent inhibits herpes virus entry mediator (HVEM)-BTLA interactions. In a further aspect, the agent decreases the level of γδT cells. In an additional aspect, the inflammatory or autoimmune disease may be psoriasis, multiple sclerosis, diabetes, dermatitis, celiac disease, cancer, sclerosis cholangitis or rheumatoid arthritis.

In an additional embodiment, the invention provides a method of modulating the level and activity of γδT cells comprising administering an agent that modulates BTLA expression or activity. In one aspect, the agent increases BTLA expression or activity and increases the level and/or activity of γδT cells. In an additional aspect, the agent increases IL-7 expression or activity or inhibits RORγt expression or activity. In a further aspect, the agent inhibits HVEM-BTLA interactions. In one aspect, the agent decreases BTLA expression or activity and decreases the level and/or activity of γδT cells. In another aspect, the agent inhibits IL-7 expression or activity or increases RORγt expression or activity.

In one embodiment, the invention provides for a method of modulating γδT cell production of IL-17 or TNF comprising administering an agent that modulates BTLA expression or activity. In an aspect, the agent increases BTLA expression or activity and decreases γδT cell production of IL-17 or TNF. In an additional aspect, the agent increases IL-7 expression or activity or inhibits RORγt expression or activity. In an aspect, the agent inhibits HVEM-BTLA interaction. In one aspect, the agent inhibits BTLA expression or activity and increases γδT cell production of IL-17 or TNF. In a further aspect, the agent inhibits IL-7 expression or activity or increases RORγt expression or activity.

In a further embodiment, the present invention provides a method of screening for an agonist of BTLA comprising contacting a lymphocyte culture with an agent; determining the level of γδT cells in the culture; and comparing the level of γδT cells with the level of γδT cells in a lymphocyte culture not contacted with the agent, wherein an increased level of γδT cells in the lymphocyte culture contacted with the agent indicates that the agent is a BTLA agonist. In one aspect, the lymphocyte culture is enriched for innate lymphoid cells (ILCs) and CD27$^-$ γδT cells. In another aspect, the level of γδT cells is determined by identifying cells with γδT cell surface markers. In a further aspect, the cell surface markers may be BTLA, CD27 or RORγt.

BRIEF DESCRIPTION OF THE DRAWINGS

FIGS. 1A-I show BTLA expression in γδT cells. (A) Expression of RORγt and TCRβ. (B) Expression of BTLA and TCR-β in RORγt-gated cells. (C) Expression of TCRγδ and TCRβ in RORγt-gated cells. (D) Mean fluorescent intensity (MFI) for BTLA expression in TCRγδ$^+$ and TCRβ$^+$ cells. (E) Expression of BTLA and RORγt in γδT cells. (F) MFI for BTLA expression in RORγt$^-$ and RORγt$^+$ γδT cells. (G) Expression of CD27 and RORγt in γδT cells. (H) Expression of BTLA and CD27 in RORγt$^-$ (left) and RORγt$^+$ (right) γδT cells. (I) MFI for BTLA expression in CD27$^+$RORγt$^-$, CD27$^+$RORγt$^+$ and CD27$^-$RORγt$^+$ γδT cells.

FIGS. 2A-I show that RORγt is a transcriptional repressor of Btla. (A) Expression of RORγt and CD127 lymphocytes from the iLN (left) and the Peyer's patches (PP) (right) of Rorc(t)$^{gfp/+}$ mice. (B) MFI for RORγt-GFP expression in iLNγδT cells and PP ILCs. (C) MFI for BTLA expression in RORγt$^+$ γδT cells and ILCs. (D) Expression of BTLA and GFP in cells transduced with pMSCV-IRES-GFP-RORγt retrovirus (RV-RORγt) or with empty retrovirus (RV). (E) mRNA levels (relative to L32) of Rorc and Btla in FACS-sorted RORγt$^-$ GFP$^-$, RORγt-GFP$^{Low}$ and RORγt-GFP$^{High}$ cells transduced with RV-RORγt. (F) sequence similarity between the promoter regions of the human and mouse BTLA coding genes and graphical representation of the conserved RORγt binding sites and their positions relative to the transcription start (indicated by arrow). (G) PCR analysis of RORγt binding sites −49 and −369 following a ChIP assay with anti-RORγ or control IgG in RV-RORγt transduced cells. (H) Mouse Btla promoter reporter activity in Jurkat cells co-transfected with wild type or mutated promoter. (I) Mouse Btla promoter reporter activity in Jurkat cells co-transfected with wild-type promoter in the presence or absence of wild-type (wt) or Activation Function domain 2 (AF2)-mutant or DNA Binding Domain (DBD)-mutant RORγt.

FIGS. 4A-K show that IL-7 and BTLA form a negative feedback loop. (A) Expression of CD27 and Vγ2 with or without IL-7 in TCRγδ$^+$TCRβ$^-$ gated cells. (B) Percentage of Btla$^{+/+}$ and Btla$^{-/-}$ CD27$^-$ γδT cells with or without IL-7. (C-F) The fold difference in γδT cell cellularity as defined by the ratio of cell number with or without IL-7. (C) Vγ2$^-$CD27$^-$ γδT cells, (D) Vγ2$^+$CD27$^-$ γδT cells, (E) Vγ2$^-$CD27$^+$ γδT cells, (F) Vγ2$^+$CD27$^+$ γδT cells. (G) Expression of BTLA and RORγt in iLN γδT cells (top) and PP ILCs (bottom) with or without IL-7. (H) Numbers of BTLA$^+$ iLN γδT cells. (I) MFI for BTLA expression in iLN γδT cells. (J) Numbers of BTLA$^+$ PP ILCs. (K) MFI for BTLA expression in PP ILCs.

FIGS. 5A-D show that BTLA regulates γδT cell production of IL-17 and TNF. (A, C) Expression of IL-17 (A) or TNF (C) and CD27 with (bottom) or without (top) IL-7. (B, D) Percentage of IL-17$^-$ (B) or TNF (D) expressing CD27$^-$ (top) or CD27$^+$ (bottom) Btla$^{+/+}$ and Btla$^{-/-}$ γδT cells with or without IL-7.

FIGS. 6A-F show that Btla$^{-/-}$ animals are susceptible to dermatitis. (A) presence of inflamed skin in IMQ-treated Btla$^{-/-}$ mice. (B) Thickness of the epidermis in IMQ-treated mice. (C) H&E staining of skin sections from untreated or IMQ-treated Btla$^{+/+}$ and Btla$^{-/-}$ mice. (D) Percentage of epidermal γδT cells (TCRγδ$^+$Vg3$^-$) in untreated or IMQ-treated mice. (E) Percentage of epidermal Ly6G$^+$ cells in IMQ-treated Btla$^{+/+}$ and Btla$^{-/-}$ mice. (F) Percentage of lymph node (LN) CD27$^-$ γδT cells in IMQ-treated Btla$^{+/+}$ and Btla$^{-/-}$ mice.

FIGS. 7A-E show that treatment with an agonistic anti-BTLA inhibits γδT cells and restricts dermatitis. (A) percentage of lymph node Vγ2$^+$CD27$^-$ γδT cells in naïve (−) and IMQ- or IMQ+6A6-treated animals. (B) percentage of lymph node Vγ2$^+$IL-17$^+$CD27$^-$γδT cells in naïve (−) and IMQ- or IMQ+6A6-treated animals. (C) percentage of skin Vγ2$^+$CD27$^-$ γδT cells in naïve (−) and IMQ- or IMQ+6A6-treated animals. (D) H&E staining of skin sections from IMQ- or IMQ+6A6-treated animals. (E) Thickness of the epidermis in IMQ- or IMQ+6A6 treated animals.

FIGS. 8A-I show BTLA expression in mouse and human RORγt$^-$ ILCs. (A) Expression of RORγt and TCRβ. (B) Expression of BTLA and TCRβ in RORγt-gated cells. (C) Expression of TCRγβ and TCRβ in RORγt-gated cells. (D) MFI for BTLA expression in ILCs and TCRβ$^+$ cells. (E) Expression of BTLA in RORγt$^+$ ILCs from PP or RORγt$^+$ γδT cells from the iLN. (F) Expression of BTLA in RORγt$^+$ and RORγt$^-$ Thy1.2$^+$CD127$^+$ ILCs in the PP. (G) Expression of CD117 and BTLA in human CD3$^+$ and CD3$^-$ peripheral blood lymphocytes gated on CD127$^+$CCR6$^+$ cells. (H-I) Expression of IL-22 and BTLA (H) or CD117 and CD3 (I) in human tonsil lymphocytes.

FIGS. 9A-B show expression of HVEM in different lymphoid tissues as well as in Btla$^{-/-}$ and Btla$^{/1+}$ γδT cells. (A) Expression of HVEM in RORγt$^+$TCRβ$^-$ and RORγt$^+$TCRβ$^+$ in the spleen, iLN, mesenteric LN (mLN), PP and lamina propria (LP) of the small intestine. (B) Expression of HVEM in Btla$^{+/+}$ and Btla$^{-/-}$ γδT cells.

FIGS. 10A-D show BTLA expression in TH17 and double positive thymocytes. (A) IL-17 staining of mouse spleen CD4$^+$ T cells activated under non-polarizing (THO) or TH17-polarizing conditions and re-stimulated with PMA+ionomycin. (B) Expression of BTLA in THO and TH17 cells. (C) MFI for BTLA expression in THO and TH17 cells. (D) Expression of RORγt and BTLA in DP (CD4$^+$CD8$^+$ double-positive), CD4$^+$ and CD8$^+$ single positive thymocytes isolated from Rorc(t)$^{gfp/-}$ mice.

FIGS. 11A-D demonstrate that RORγt represses BTLA. (A) Expression of BTLA on a RORγt knockdown. (B) mRNA and surface expression of BTLA in digoxin treated RORγt expressing Jurkat cells. (C) qPCR analysis using primers specific for the RORγt binding sites −49 and −369. (D) Mouse Btla promoter reporter activity in Jurkat cells co-transfected with wild type or mutated promoter, and 10 ng RORγt expressing plasmid.

FIGS. 13A-C show RORγt mutations. (A) Amino acid sequence of RORγt (SEQ ID NO: 21) indicating its three functional domains. (B) RORγt truncation mutants. (C) Expression of RORγt by antibody staining over RORγt-GFP expression in 293T.

FIGS. 14A-I show that BTLA negatively regulates thymic γδT cells. (A) Gating strategy for identifying γδT cell subsets in thymocytes. (B) Expression of BTLA in CD27$^+$ and CD27$^-$ γδT cells. (C) MFI for BTLA expression in CD27$^+$ and CD2T γδT cells. (D-H) Numbers of γδT cells. (D) total, (E) CD27$^+$, (F) CD2T, (G) CD27$^-$Vγ2$^+$, (H) CD27$^-$Vγ2$^-$. (I) Distribution of thymic CD27$^+$, CD27$^-$Vγ2$^+$, and CD27$^-$Vγ2$^-$ γδT cells in Btla$^{+/+}$ (top) and Btla$^{-/-}$ (bottom) mice.

FIGS. 15A-C show that BTLA affects the homeostasis of peripheral but not gut ILCs. (A) FACs analysis of lymphocytes from the PP of Btla$^{+/+}$ and Btla$^{-/-}$ mice e enriched for ILCs. (B) Schematic of the experimental method used for (C). (C) Lymphocytes isolated from the spleens of Rag2$^{-/-}$ Ilrg$^{-/-}$ mice reconstituted with Btla$^{+/+}$ (CD45.1$^+$) or Btla$^{-/-}$ (CD45.1$^-$).

FIG. 16 shows expression of CD127 in Btla$^{+/+}$ and Btla$^{-/-}$ γδT cells.

FIG. 19 shows the gating strategy for the analysis of non-DETC γδT cells in the skin.

FIGS. 20A-C demonstrate that CD4$^+$ γδT cells are not involved in IMQ-induced inflammation of Btla$^{-/-}$ animals. (A) Percentage of TCRγ$^+$ cells in the epidermis of Btla$^{+/+}$ and Btla$^{-/-}$ mice before and after IMQ treatment. (B) CD4 T cells were depleted in IMQ treated Btla$^{-/-}$ mice after a single injection of anti-GK1.5. (C) H&E staining of skin tissue indicating no difference in IMQ treated Btla$^{-/-}$ mice that were CD4-sufficient or CD4-depleted.

DETAILED DESCRIPTION

Figures 1, 2F:
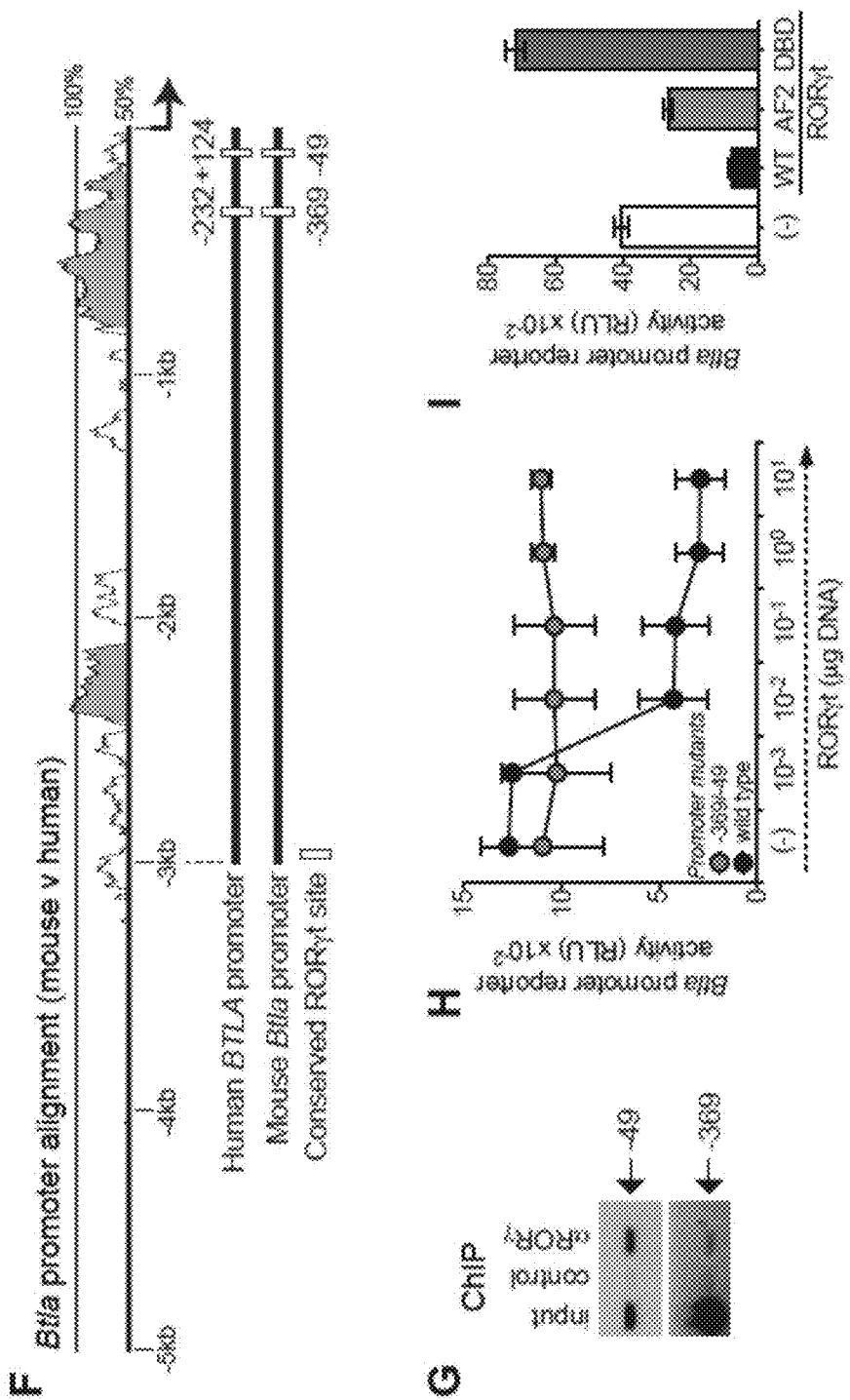

The present invention relates to the discovery that BTLA, IL-7 and RORγt modulate the activity and level of γδT cells. Specifically, the present invention provides methods of modulating γδT cell homeostasis and function by regulating expression of BTLA. The present invention further provides agents which modulate the activity and expression of BTLA, RORγt and IL-7 and methods for screening of such agents. The present invention also provides methods for treating autoimmune or inflammatory diseases using modulators of BTLA, RORγt and IL-7.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. T cells mature in the thymus (although some also mature in the tonsils). There are several subsets of T cells, each with a distinct function.

T helper cells (TH cells or CD4+ T cells) assist in immunologic processes, including maturation of B cells into plasma cells and memory B cells, and activation of cytotoxic T cells and macrophages. CD4+ T cells become activated when they are presented with peptide antigens by MHC class II molecules, which are expressed on the surface of antigen-presenting cells (APCs). These cells can differentiate into one of several subtypes, including TH1, TH2, TH3, TH17, Th9, or TFH, which secrete different cytokines to facilitate a different type of immune response.

Cytotoxic T cells (TC cells, or CTLs) destroy virally infected cells and tumor cells, and are also implicated in transplant rejection. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells).

Regulatory T cells (T reg cells) are crucial for the maintenance of immunological tolerance. T reg cells shut down T cell-mediated immunity toward the end of an immune reaction and to suppress auto-reactive T cells that escaped the process of negative selection in the thymus. Two major classes of CD4+ T reg cells have been described: Foxp3+ T reg cells and Foxp3− Treg cells. Regulatory T cells can develop either during normal development in the thymus, and are then known as thymic Treg cells, or can be induced peripherally and are called peripherally derived Treg cells.

Natural killer T cells (NKT cells) bridge the adaptive immune system with the innate immune system. NKT cells recognize glycolipid antigen presented by CD1d. Once activated, these cells can perform functions ascribed to both Th and Tc cells (i.e., cytokine production and release of cytolytic/cell killing molecules) and are able to recognize and eliminate some tumor cells and cells infected with herpes viruses.

Gamma delta T cells (γδT cells) represent a small subset of T cells that possess a distinct T cell receptor (TCR) on their surface. A majority of T cells have a TCR composed of two glycoprotein chains called α- and β-TCR chains. However, in γδT cells, the TCR is made up of one γ-chain and one δ-chain. This group of T cells is much less common in humans and mice (~2% of total T cells); and are found in the highest abundance in the gut mucosa, within a population of lymphocytes known as intraepithelial lymphocytes (IELs). The antigenic molecules that activate γδT cells are still widely unknown. However, γδT cells are not MHC restricted and seem to be able to recognize whole proteins rather than requiring peptides to be presented by MHC molecules on antigen-presenting cells. Some murine γδT cells recognize MHC class IB molecules though. Human Vγ9/Vδ2 T cells, which constitute the major γδT cell population in peripheral blood, are unique in that they specifically and rapidly respond to a set of non-peptidic phosphorylated isoprenoid precursors, collectively named phosphoantigens. Phosphoantigens are produced by virtually all living cells. The most common phosphoantigens from animal and human cells (including cancer cells) are isopentenyl pyrophosphate (IPP) and its isomer dimethylallyl pyrophosphate (DMAPP). Many microbes produce the highly active compound hydroxy-DMAPP (HMB-PP) and corresponding mononucleotide conjugates, in addition to IPP and DMAPP.

B- and T-lymphocyte attenuator (BTLA) is a protein that in humans is encoded by the BTLA gene. BTLA expression is induced during activation of T cells, and BTLA remains expressed on TH1 cells but not TH2 cells. Like PD1 and CTLA4, BTLA interacts with a B7 homolog, B7H4. However, unlike PD-1 and CTLA-4, BTLA displays T cell inhibition via interaction with tumor necrosis family receptors (TNF-R), not just the B7 family of cell surface receptors. BTLA is a ligand for herpes virus entry mediator (HVEM). BTLA-HVEM complexes negatively regulate T cell immune responses. BTLA expression also modulates the levels of γδT cells and together with IL-7 expression forms a negative feedback loop for γδT cells.

The retinoid-related orphan receptors (RORs) are members of the nuclear receptor family of intracellular transcription factors. There are three forms of ROR, ROR-α, -β, and -γ and each is encoded by a separate gene (Roca, Rorb, and Rorc respectively). The RORs are somewhat unusual in that they appear to bind as monomers to hormone response elements as opposed to the majority of other nuclear receptors which bind as dimers. The three forms of RORs fulfill a number of critical roles including: ROR-α—development of the cerebellum and lymph nodes, lipid metabolism, immune response, maintenance of bone; ROR-β—precise role unknown but highly expressed in the brain and retina; and ROR-γ—lymph node development and immune response, survival of TH17 cells. RORγt also modulates BTLA expression.

IL-7 a hematopoietic growth factor secreted by stromal cells in the bone marrow and thymus. IL-7 stimulates the differentiation of multipotent (pluripotent) hematopoietic stem cells into lymphoid progenitor cells and stimulates proliferation of all cells in the lymphoid lineage. It is important for proliferation during certain stages of B-cell maturation, T and NK cell survival, development and homeostasis. This cytokine is found to be a cofactor for V(D)J rearrangement of the T cell receptor beta (TCRβ) during early T cell development. Knockout studies in mice suggested that this cytokine plays an essential role in lymphoid cell survival. IL-7 binds to the IL-7 receptor resulting in a cascade of signals important for T-cell development within the thymus and survival within the periphery. IL-7 expression also modulates the expression of BTLA and together with BTLA expression forms a negative feedback loop for γδT cells.

Tumor necrosis factor (TNF) is an adipokine involved in systemic inflammation. It is produced chiefly by activated macrophages. The primary role of TNF is in the regulation of immune cells. TNF is able to induce fever, apoptotic cell death, cachexia, inflammation and to inhibit tumorigenesis and viral replication and respond to sepsis via IL1 & IL6 producing cells. Dysregulation of TNF production has been implicated in a variety of human diseases including Alzheimer's disease, cancer, major depression and inflammatory bowel disease (IBD). TNF is also produced by CD27−γδT cells.

Interleukin 17A (IL-17) acts as a potent mediator in delayed-type reactions by increasing chemokine production in various tissues to recruit monocytes and neutrophils to the site of inflammation. IL-17 is produced by T-helper cells and is induced by IL-23 which results in destructive tissue damage in delayed-type reactions. IL 17 as a family functions as a proinflammatory cytokine and IL 17 acts synergistically with tumor necrosis factor and ILL Numerous immune regulatory functions have been reported for the IL-17 family of cytokines most notably its involvement in inducing and mediating proinflammatory responses. IL-17 function is also essential to TH17 cells. As a result of these roles, the IL-17 family has been linked to many immune/autoimmune related diseases including rheumatoid arthritis, asthma, lupus, allograft rejection, anti-tumour immunity and recently Psoriasis. IL-17 is also produced by CD27$^+$γδT cells.

γδT cells play a critical role in the immune system inflammatory response and have been implicated in a variety of inflammatory and autoimmune diseases. For example, it has been shown that γδT cells play a critical role in establishing skin inflammation, psoriasis, multiple sclerosis and diabetes. BTLA expression modulates the level and activity of γδT cells and is therefore a good target for treating inflammatory and autoimmune disorders. Alteration of BTLA expression can occur by mutations in ligands that bind BTLA HVEM, a ligand of BTLA, has been associated with several autoimmune related diseases including celiac disease sclerosing cholangitis and rheumatoid arthritis. Further, certain cancers are characterized by mutations in HVEM resulting in the deletion of HVEM and in increased expression of BTLA that can be agonized with an antibody or other agonist of BTLA activity to suppress cancer growth. Thus modulators of BTLA expression may enhance the ability of BTLA agonists alone or in combination with other agents to limit cancer growth and lethality. Such cancers include hematologic cancers, i.e. leukemia and lymphoma and some solid tumor cancers including breast cancer, lung cancer and colon cancer. Hematologic cancers include acute lymphoblastic leukemia, acute myeloid leukemia, chronic lymphocytic leukemia, chronic myelogenous leukemia, T-cell lymphoma, Hodgkin's lymphoma, non-Hodgkin's lymphoma and B cell lymphoma.

In one embodiment, the invention provides a method of treating an inflammatory or autoimmune disease in a subject in need thereof comprising administering to the subject one or more agents that modulate the level and/or activity of γδT cells, thereby treating the inflammatory or autoimmune disease. In one aspect, the agent increases B and T lymphocyte attenuator (BTLA) expression or activity. In another aspect, the agent inhibits retinoid-related orphan receptor gamma-isoform-t (RORγt) expression or activity. In an aspect, the agent increases IL-7 expression or activity. In one aspect, the agent modulates the production of IL-17 or TNF by γδT cells. In an aspect, the agent modulates the levels of RORγt$^-$ γδT cells or RORγt$^+$ γδT cells. In another aspect, one agent increases BTLA expression or activity and a second agent inhibits RORγt expression or activity. In a further aspect, the agent inhibits herpes virus entry mediator (HVEM)-BTLA interactions. In a further aspect, the agent decreases the level of γδT cells. In an additional aspect, the inflammatory or autoimmune disease may be psoriasis, multiple sclerosis, diabetes, dermatitis, celiac disease, cancer, sclerosis cholangitis or rheumatoid arthritis.

The term "agent" as used herein refers to any compound or molecule which modulates the level of γδT cells. Such agents modulate the expression or activity of BTLA, IL-7 or RORγt. An agent may be an agonist of BTLA or IL-7 or an antagonist of RORγt. An agent includes a modulator of transcription factors that affect the expression or activity of BTLA, IL-7 or RORγt. Such transcription factors include NFAT, AP-1, Fos, NF κB, STAT1, STAT3, STAT5, Bcl6, Dec1, Nfil3, Gfil1 and PZLF. The agent can be a chemical compound, including a small molecule, or a biologic molecule, including a protein, an antibody or fragment thereof, a peptide, an RNAi, an siRNA or an antisense molecule. An agent can be identified by any method known in the art.

The term "polypeptides/protein" as used herein, refers to macromolecules comprising linear polymers of amino acids which may act in biological systems, for example, as structural components, enzymes, chemical messengers, receptors, ligands, regulators, hormones, and the like. Such polypeptides/proteins would include functional protein complexes, such as antibodies.

The term "antibody" as used herein, refers to an immunoglobulin or a part thereof, and encompasses any polypeptide comprising an antigen-binding site regardless of the source, species of origin, method of production, and characteristics. The term includes but is not limited to polyclonal, monoclonal, monospecific, polyspecific, non-specific, humanized, single-chain, chimeric, synthetic, recombinant, hybrid, mutated, and CDR-grafted antibodies. For the purposes of the present invention, it also includes, unless otherwise stated, antibody fragments such as Fab, F(ab)$_2$, Fv, scFv, Fd, dAb, and other antibody fragments that retain the antigen-binding function.

The term "small molecule" as used herein refers to compounds that are not macromolecules (see, e.g., Karp (2000) Bioinformatics Ontology 16:269-85; Verkman (2004) AJP-Cell Physiol. 286:465-74). Thus, small molecules are often considered those compounds that are less than one thousand daltons (e.g., Voet and Voet, Biochemistry, 2.sup.nd ed., ed. N. Rose, Wiley and Sons, New York, 14 (1995)). For example, Davis et al. ((2005) Proc. Natl. Acad. Sci. USA 102:5981-86) use the phrase small molecule to indicate folates, methotrexate, and neuropeptides, while Halpin and Harbury ((2004) PLos Biology 2:1022-30) use the phrase to indicate small molecule gene products, e.g., DNAs, RNAs and peptides. Examples of natural small molecules include, but are not limited to, cholesterols, neurotransmitters, and siRNAs; synthesized small molecules include, but are not limited to, various chemicals listed in numerous commercially available small molecule databases, e.g., FCD (Fine Chemicals Database), SMID (Small Molecule Interaction Database), ChEBI (Chemical Entities of Biological Interest), and CSD (Cambridge Structural Database) (see, e.g., Alfarano et al. (2005) Nuc. Acids Res. Database Issue 33:D416-24).

The terms "modulation" or "modulates" as used herein refers to an alteration in the level, expression or activity of a molecule or cell. Modulation includes increasing or decreasing the level or activity of cells including γδT cells. Modulation also includes increasing or decreasing expression or activity of BTLA, IL-7, RORγt, TNF and IL-17.

A combination of more than one agent may be used to treat an inflammatory or autoimmune disease or to modulate the level and activity of γδT cells. For example, a subject may be administered a combination of a RORγt antagonist and a BTLA agonist; a RORγt antagonist and an IL-7 agonist; or an IL-7 agonist and a BTLA agonist. In a further example, a small molecule RORγt antagonist, such as Digoxin, can be used in combination with a BTLA agonist antibody, such as (6A6).

The term "subject" as used herein refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

Autoimmune diseases arise from an abnormal immune response of the body against substances and tissues normally present in the body (autoimmunity). A major understanding of the underlying pathophysiology of autoimmune diseases has been the application of genome wide association scans that have identified a striking degree of genetic sharing among the autoimmune diseases.

Autoimmune disorders include, but are not limited to, Acute disseminated encephalomyelitis (ADEM), Addison's disease, Agammaglobulinemia, Alopecia areata, Amyotrophic lateral sclerosis (aka Lou Gehrig's disease), Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, Graves' disease, Guillain-Barré syndrome, Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease, Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Ménière's disease, Narcolepsy, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome, Schnitzler syndrome, Scleritis, Scleroderma, Serum Sickness, Sjögren's syndrome, Spondyloarthropathy, Stiff person syndrome, Still's disease, Subacute bacterial endocarditis (SBE), Susac's syndrome, Sweet's syndrome, Sydenham chorea, Sympathetic ophthalmia, Systemic lupus erythematosus, Takayasu's arteritis, Temporal arteritis, Thrombocytopenia, Tolosa-Hunt syndrome, Transverse myelitis, Ulcerative colitis, Undifferentiated spondyloarthropathy, Urticarial vasculitis, Vasculitis, Vitiligo, Wegener's granulomatosis.

Inflammatory disease are a large group of disorders that underlie a vast variety of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease. A large variety of proteins are involved in inflammation, and any one of them is open to a genetic mutation which impairs or otherwise dysregulates the normal function and expression of that protein. Examples of disorders associated with inflammation include Acne vulgaris, Asthma, Autoimmune diseases, Celiac disease, Chronic prostatitis, Glomerulonephritis, Hypersensitivities, Inflammatory bowel diseases, Pelvic inflammatory disease, Reperfusion injury, Rheumatoid arthritis, Sarcoidosis, Transplant rejection, Vasculitis, Interstitial cystitis, Atherosclerosis, Allergies, Myopathies, leukocyte defects and cancer.

In an additional embodiment, the invention provides a method of modulating levels of γδT cells comprising administering an agent that modulates BTLA expression or activity. In one aspect, the agent increases BTLA expression or activity and increases the level and/or activity of γδT cells. In an additional aspect, the agent increases IL-7 expression or activity or inhibits RORγt expression or activity. In a further aspect, the agent inhibits HVEM-BTLA interactions. In one aspect, the agent decreases BTLA expression or activity and decreases the level and/or activity of γδT cells. In another aspect, the agent inhibits IL-7 expression or activity or increases RORγt expression or activity.

A combination of more than one agent may be used to modulate BTLA expression or activity. For example, a combination of a RORγt antagonist and a BTLA agonist; a RORγt antagonist and an IL-7 agonist; or an IL-7 agonist and a BTLA agonist may be administered. In a further example, a small molecule RORγt antagonist, such as Digoxin, can be used in combination with a BTLA agonist antibody, such as (6A6).

In one embodiment, the invention provides for a method of modulating γδT cell production of IL-17 or TNF comprising administering an agent that modulates BTLA expression or activity. In an aspect, the agent increases BTLA expression or activity and decreases γδT cell production of IL-17 or TNF. In an additional aspect, the agent increases IL-7 expression or activity or inhibits RORγt expression or activity. In an aspect, the agent inhibits HVEM-BTLA interaction. In one aspect, the agent inhibits BTLA expression or activity and increases γδT cell production of IL-17 or TNF. In a further aspect, the agent inhibits IL-7 expression or activity or increases RORγt expression or activity.

In a further embodiment, the present invention provides a method of screening for an agonist of BTLA comprising contacting a lymphocyte culture with an agent; determining the level of γδT cells in the culture; and comparing the level of γδT cells with the level of γδT cells in a lymphocyte culture not contacted with the agent, wherein an increased level of γδT cells in the lymphocyte culture contacted with the agent indicates that the agent is a BTLA agonist. In one aspect, the lymphocyte culture is enriched for innate lymphoid cells (ILCs) and CD27⁻ γδT cells. In another aspect, the level of γδT cells is determined by identifying cells with γδT cell surface markers. In a further aspect, the cell surface markers may be BTLA, CD27 or RORγt.

In the Examples below, it is demonstrated that BTLA regulates the homeostasis of γδT cells and ILCs in lymphoid tissues. RORγt intrinsically suppresses BTLA mRNA transcription, limiting BTLA translation and membrane expression, whereas IL-7 increases BTLA membrane expression to counterbalance RORγt. Our observations define BTLA as a key component in homeostasis that controls the number of innate lymphocytes in secondary lymphoid tissues. BTLA also controls IL-7-dependent proliferation and production of IL-17 and TNF in mature lymph node γδT cells. Thus, in response to inflammatory stimuli, BTLA provides a brake to autoimmune pathology that is revealed in BTLA-deficient animals, which contain a dysregulated proportion of inflammatory γδT cells, correlating with increased susceptibility to dermatitis.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

RORγt⁺ Lymphocytes Express Reduced Levels of BTLA

In order to define the expression of BTLA in innate lymphocyte populations Rorc reporter mice expressing GFP (Rorc(t)$^{gfp/+}$ mice) were used to discriminate cellular subsets. Within the RORγt population of inguinal lymph nodes (iLN), we distinguished BTLA⁺TCRβ⁺ and BTLA$^{low}$TCRβ⁻ cells (FIG. 1A-B). Among RORγt⁺ cells the BTLA$^{low}$TCRβ⁻ population comprised >95% of γδT cells (FIG. 1C) and in general all γδT cells (RORγt⁺ and RORγt⁻ alike) expressed significantly lower (4-fold) level of BTLA than conventional T cells (FIG. 1D). However, there was a significant difference in surface BTLA between the RORγt⁺ and RORγt⁻ γδT cells (FIG. 1E-F). Even lower levels of BTLA were identified in RORγt⁺ γδT cells lacking CD27, indicating an additional level of regulation to BTLA expression (FIG. 1G-I). Among lymph node RORγt⁺ cells, the CD27⁻ γδT cell subset, which is associated with IL-17 production and autoimmune pathology, expressed the lowest levels of BTLA.

It was observed that both BTLA$^{low}$TCRβ⁻ and BTLA⁺ TCRβ⁺ RORγt⁺ populations in intestinal Peyer's patches (PP) (FIG. 8A-B). In contrast to iLN, more than 90% of the BTLA$^{low}$TCRβ⁻ lymphocytes were ILCs, defined by the lack of TCRγδ expression (FIG. 8C). BTLA levels in ILCs were also significantly reduced compared with conventional TCRβ⁺ T cells (FIG. 8D), and were 2-fold reduced compared to iLN RORγt⁺ γδT cells (FIG. 8E). Furthermore, it was observed that the lowest surface BTLA expressed in RORγt⁺ ILCs compared with RORγt⁻ Thy1.2⁺CD127⁺ cells (FIG. 8F). In contrast, HVEM levels were nearly the same between TCRβ⁻ and TCRβ⁺ cells in all lymphoid organs (FIG. 9).

In addition, it was found that human innate lymphoid cells in blood (CD3⁻CD117⁺) expressed substantially lower BTLA levels than conventional T cells (CD3⁺CD117⁻ cells) (FIG. 8G), while IL-22-producing CD117⁺ ILCs from human tonsils had undetectable surface BTLA (FIG. 8H-I). We found down-regulation of BTLA in RORγt⁺ differentiated TH17 compared to unpolarized cells, and in double-positive thymocytes compared to single positive (FIG. 10). To a first approximation, the trend to less BTLA expression in RORγt⁺ cells is conserved in all lymphoid compartments examined between human and mouse.

Example 2

RORγt is a Transcriptional Repressor of Btla

The selective down modulation of BTLA within RORγt⁺ innate lymphocytes in mouse and human suggested a potential regulatory interaction. It was observed that the greatest expression of RORγt in PP derived ILCs, 5.5-fold more than in γδT cells from the iLN (FIG. 2A-B). Together the reduced levels of BTLA in ILCs (FIG. 8E and FIG. 2C), this data suggests and inverse correlation between RORγt and BTLA expression levels. To test whether RORγt antagonized BTLA expression we ectopically expressed RORγt using an IRES-GFP retrovirus in a BTLA⁺ mouse T cell line. Interestingly, it was found that ectopic expression of high levels of RORγt resulted in decreased BTLA expression (FIG. 2D-E). Furthermore, knock-down of RORγt in these cells restored BTLA expression (FIG. 11A) whereas treatment of RORγt-expressing Jurkat cells with the RORγt inhibitor digoxin induced expression of BTLA both at the protein and mRNA levels (FIG. 11B), indicating active RORγt-dependent suppression of BTLA.

Figure 12:
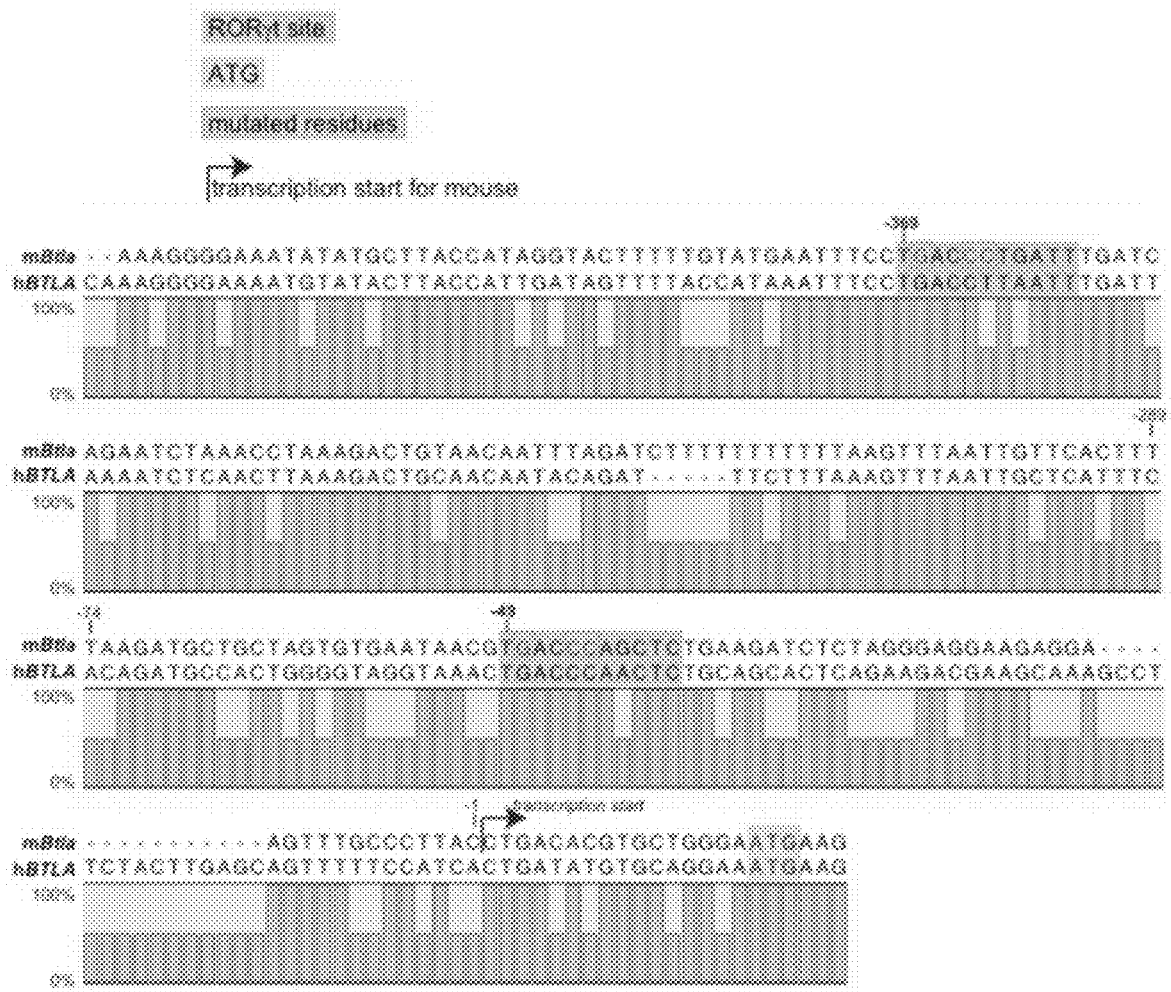
FIG. 12 shows aligned sequences of human (SEQ ID NO: 20) and mouse (SEQ ID NO: 19) BTLA promoter regions indicating the conserved RORγt binding sites as well as the mouse BTLA promoter mutants.
Figure 13A:
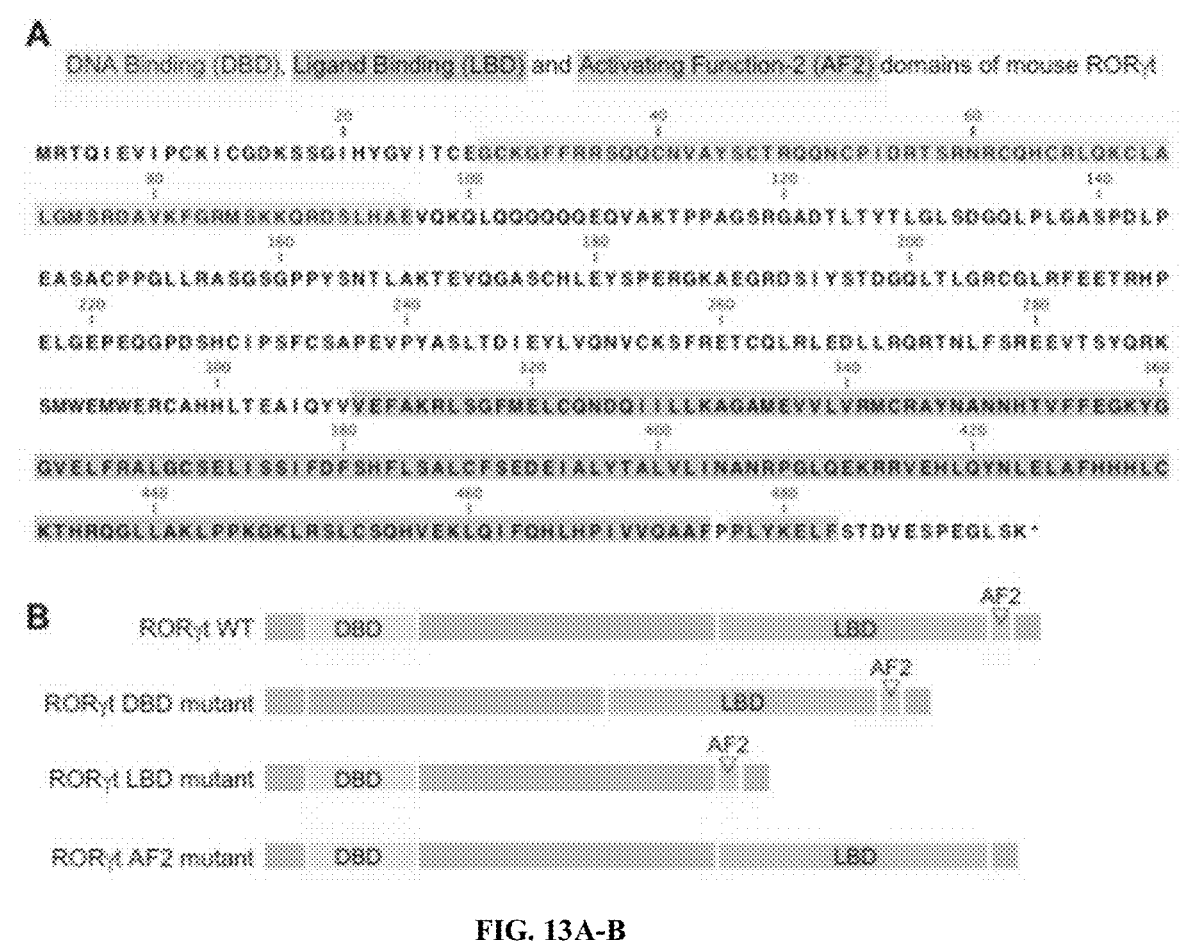
Figure 13C:
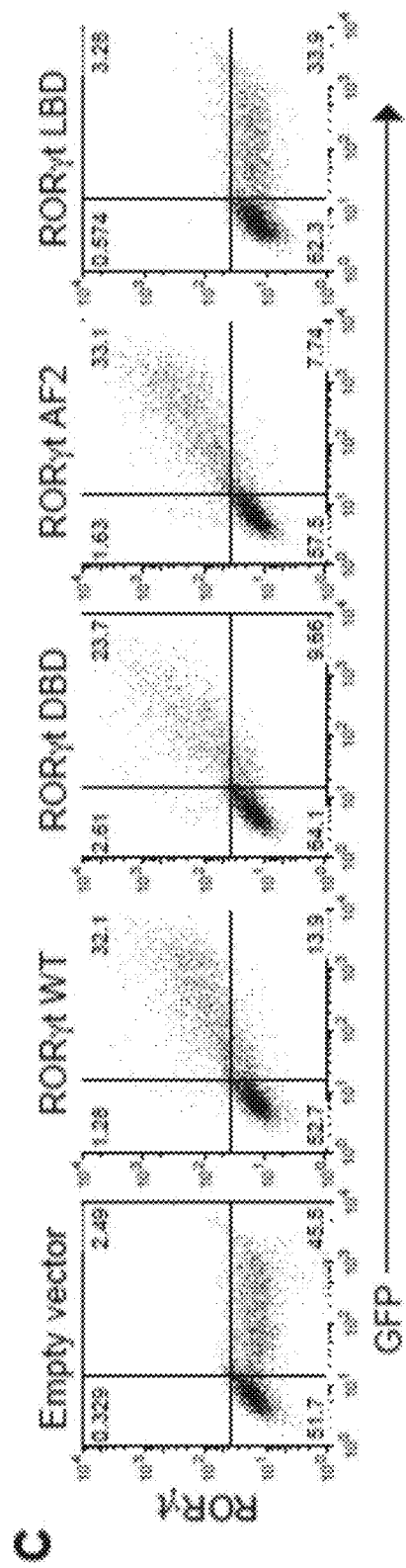

In order to determine whether RORγt directly repressed BTLA transcription we analyzed the promoters of mouse and human BTLA for conserved regulatory regions. It was found that two conserved canonical RORγt binding sites located at −232 and +124 in the human and at −369 and −49 in the mouse BTLA genes (FIGS. 2F & 12). Next, it was determined whether RORγt bound these sites by PCR amplification of chromatin immunoprecipitations (ChIP) prepared from RORγt transfectants (FIG. 2D). Significantly, both conserved sites in the mouse promoter were precipitated with RORγt (FIG. 2G), although the −49 amplified a stronger signal (FIG. 11C), which was detectable in primary mouse thymocytes (FIG. 11C). Next the proximal 0.5 kb Btla promoter was cloned into a luciferase reporter to determine how RORγt regulates promoter activity. In this regard, titrating quantities of RORγt suppressed activity of the wild-type promoter, but not a promoter with mutations at positions −369 and −49 (FIG. 2H), directly demonstrating that RORγt can function as a transcriptional repressor for BTLA (FIG. 2H). Interestingly, while the −369 site contributes more to BTLA suppression, mutation of both sites is required for optimal BTLA promoter activity (FIG. 11D). Next it was determined how RORγt mediates repressive activity by truncating either its DBD, or its AF2 domain, which may recruit transcriptional repressors (FIG. 13). Notably, BTLA promoter activity was partially restored when the RORγt AF2 region was truncated, and enhanced when the DBD regions were truncated (FIG. 2I). Thus, regulation of Btla requires RORγt binding to the promoter as well as interactions with a transcriptional co-repressor.

Example 3

BTLA Negatively Regulates Homeostasis of γδT Cells in Lymph Nodes and Thymus

Figure 3I:
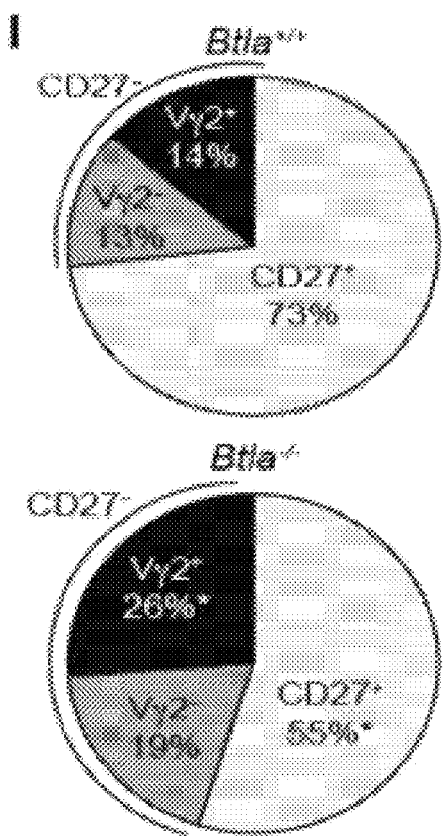
FIGS. 3A-N show that BTLA negatively regulates the homeostasis of γδT cells in lymph nodes. (A) Expression of CD27 and Vγ2 in TCRγδ$^+$TCRβ$^-$ gated cells from Btla$^{+/+}$ and Btla$^{-/-}$ mice. (B) Ratio of CD27$^-$:CD27$^+$γδT cells in Btla$^{+/+}$ and Btla$^{-/-}$ mice. (C) histograms indicate the increase in CD27$^-$Vγ2$^+$ cells in Btla$^{-/-}$ mice. (D-H) Numbers of γδT cells. (D) total, (E) CD27$^-$, (F) CD27$^+$, (G) CD27$^-$Vγ2$^-$, (H) CD27$^-$Vγ2$^+$. (I) Distribution of CD27$^+$, CD27$^-$Vγ2$^+$ and CD27$^-$Vγ2$^-$ γδT cells in Btla$^{+/+}$ (top) and Btla$^{-/-}$ (bottom) mice. (J) FACS plot indicates frequencies of γδT cell subsets in TCRγδ$^+$TCRβ$^-$ gated cells. (K) Percentage of CD45.2$^+$ Btla$^{-/-}$ and CD45.2$^-$Btla$^{+/+}$ total γδT cells in the blood. (L) Percentage of CD45.2$^+$Btla$^{-/-}$ and CD45.2$^-$Btla$^{+/+}$ γδT cell subsets in the blood. (M) Frequencies of CD45.2$^+$ Btla$^{-/-}$ and CD45.2$^-$ Btla$^{+/+}$ CD27$^+$ γδT cell subsets in iLN. (N) Frequencies of CD45.2$^+$Btla$^{-/-}$ and CD45.2$^-$Btla$^{+/+}$ CD27$^-$ γδT cell subsets in iLN.

It was determined whether the regulation of BTLA by RORγt resulted in altered distribution of γδT cell subsets in the iLN. Among γδT cells it was observed that an increase in the frequency of CD27$^-$ cells in BTLA-deficient iLN compared to wild-type (FIG. 3A-B), with a more pronounced skewing towards Vγ2-expressing cells, possibly reflecting unrestricted embryonic development of these cells in the absence of BTLA (FIG. 3C). Additionally in BTLA-deficient iLN we observed significantly increased numbers of the CD27$^-$ γδT cell subsets, while CD27$^+$ γδT cells trended towards lower numbers and total γδT cell numbers were not different between wild-type and Btla$^{-/-}$ mice (FIG. 3D-H). Together these data indicate that BTLA controls cell-intrinsic expansion of CD27$^-$ cells within the γδT cell niche. This increase in CD27$^-$ numbers resulted in a significant redistribution of the major γδT cell subsets (FIG. 3I).

In order to determine whether expansion of CD27$^-$ γδT cells in the periphery of BTLA-deficient animals originated during development, we assessed the levels of BTLA in thymic γδT cell subsets. In this regard, the CD27$^-$ subset showed lower BTLA expression than the CD27$^+$ subset, similar to that in lymph nodes (FIG. 14A-C). Interestingly, thymic TCRγδ$^+$ cell numbers were significantly increased in BTLA-deficient mice independent of whether they expressed CD27 and there was no change in the distribution of γδT cell subsets (FIG. 14D-I). Thus, while BTLA restricts the expansion of all thymic γδT cells, this does not explain the specific expansion of CD27$^-$ γδT cells in the periphery.

It was examined to determine whether BTLA-deficiency conferred a competitive advantage to γδT cells undergoing homeostatic expansion following bone marrow reconstitution of irradiated animals. significantly increased proportions of BTLA-deficient γδT cells were observed among circulating lymphocytes at five weeks post transfer, demonstrating that BTLA-deficient progenitors outcompeted their wild-type counterparts within these niches (FIG. 3J-L). In addition, Btla$^{-/-}$ γδT cell subsets outcompeted their wild-type counterparts within the lymph nodes of reconstituted animals (FIG. 3M-N). However, within chimeras reduced numbers of Vγ2$^+$CD27$^-$ γδT cells from either donor were observed, which may reflect suboptimal development in the absence of an embryonic environment.

In addition, the number of ILCs resident within gut associated lymphoid tissues did not differ between wild-type and BTLA-deficient mice (FIG. 15A). However, within mixed bone marrow chimeric mice, we observed increased numbers of Btla$^{-/-}$ ILCs in the spleens of recipient mice (Btla$^{-/-}$:Btla$^{+/+}$ ratio of 1.8) (FIG. 15B-C), indicating that BTLA deficiency provided a competitive growth advantage compared to their wild-type counterparts.

Example 4

IL-7 and BTLA Form a Negative Feedback Loop

The elevated numbers of CD27$^-$ γδT cells in BTLA-deficient mice could be partially explained by defective thymic development, however the increased frequency of the CD27$^-$ subset was specific to regional lymph nodes. It was reasoned that expansion of CD27$^-$ γδT cells in BTLA-deficient mice in peripheral lymphoid organs may be due to unrestricted IL-7 receptor signaling since IL-7 is critical for γδT cell homeostasis and preferentially affects the CD27$^-$ subset. In this regard, sustained viability of IL-7 treated γδT cells were observed within lymph node lymphocytes cultured ex vivo as compared to untreated cultures (FIG. 4A). Furthermore, BTLA-deficient γδT cells were hyper-responsive to IL-7 treatment, particularly within the CD27$^-$ subset as measured by their increased frequency upon IL-7 stimulation compared to wild-type controls (FIG. 4B) and their enhanced ability to persist after four days in culture (FIG. 4C-F), which was not due differences in CD127 expression levels (FIG. 16). Thus, BTLA restricts γδT cell responsiveness to IL-7.

Figure 17:
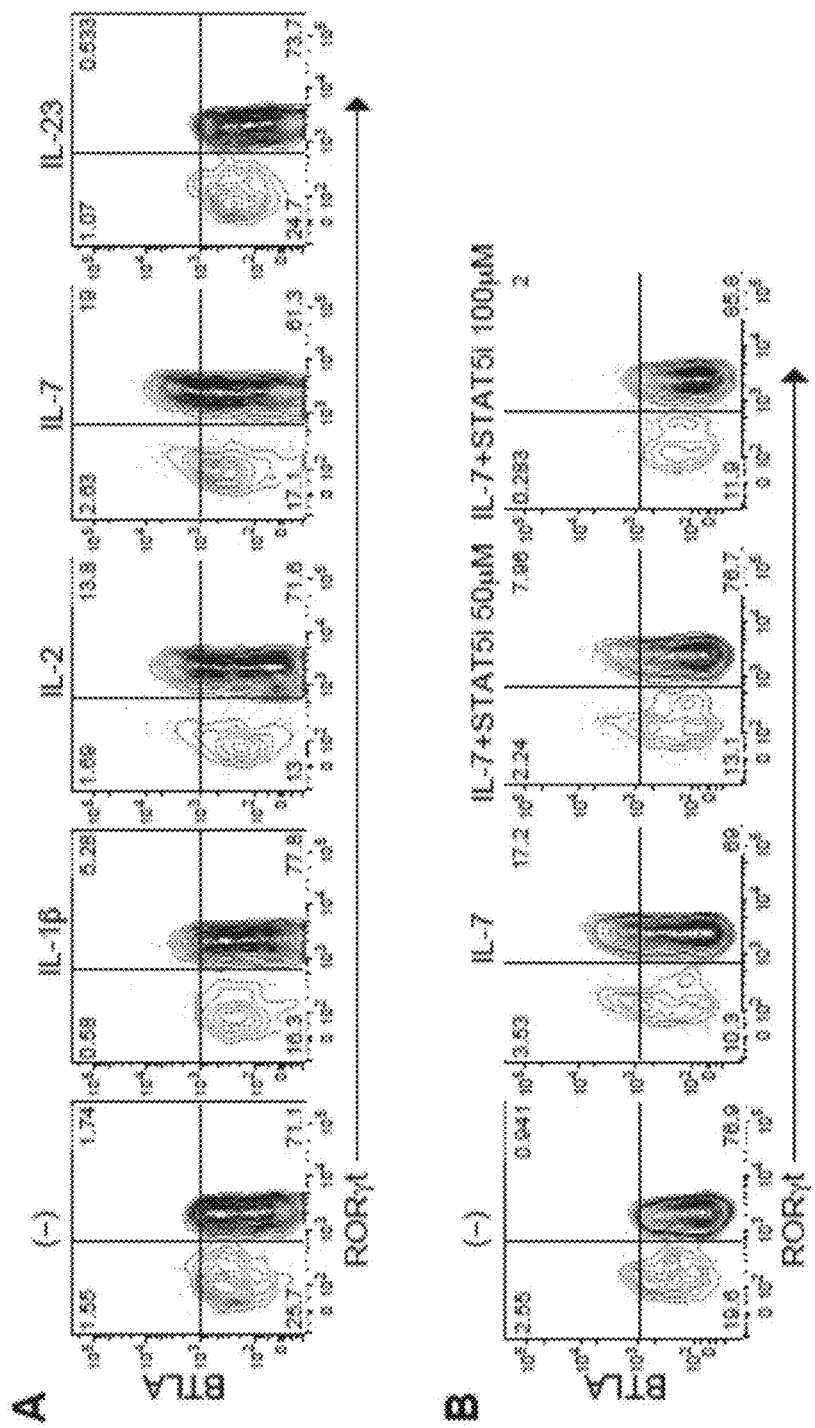
FIGS. 17A-B show expression of BTLA on RORγt$^+$ γδT cells after culture with activating cytokines (A) Cytokine or (B) IL-7 with or without STAT-inhibitor (STAT5i) cultured lymphocytes from the iLN of Rorc(t)$^{gfp/+}$ mice enriched for CD27$^-$ γδT cells.

It has been shown that activation induced regulation of BTLA expression in a cell-specific manner. It was assessed to determine whether IL-7 stimulation itself altered BTLA levels in γδT cells or ILCs by culturing iLN and PP lymphocytes from Rorc(t)$^{gfp/+}$ mice in the presence of IL-7 and analyzed BTLA expression two days later. Compared to untreated controls, IL-7 induced a higher number of BTLA$^+$ cells and increased surface BTLA expression in both γδT cells and ILCs (FIG. 4G-K). Additionally, it was found that BTLA expression in γδT cells was induced with IL-2, and that IL-7 up-regulation of BTLA was STAT5-dependent (FIG. 17A-B). In contrast, IL-23 and IL-1β, two potent γδT cell activators, had either no or only a minimal effect in BTLA induction (FIG. 17A). Thus, IL-7 signaling induces BTLA expression, which in turn limits IL-7-dependent responses.

Example 5

BTLA Regulates γδT Cell Production of IL-17 and TNF

Figure 18:
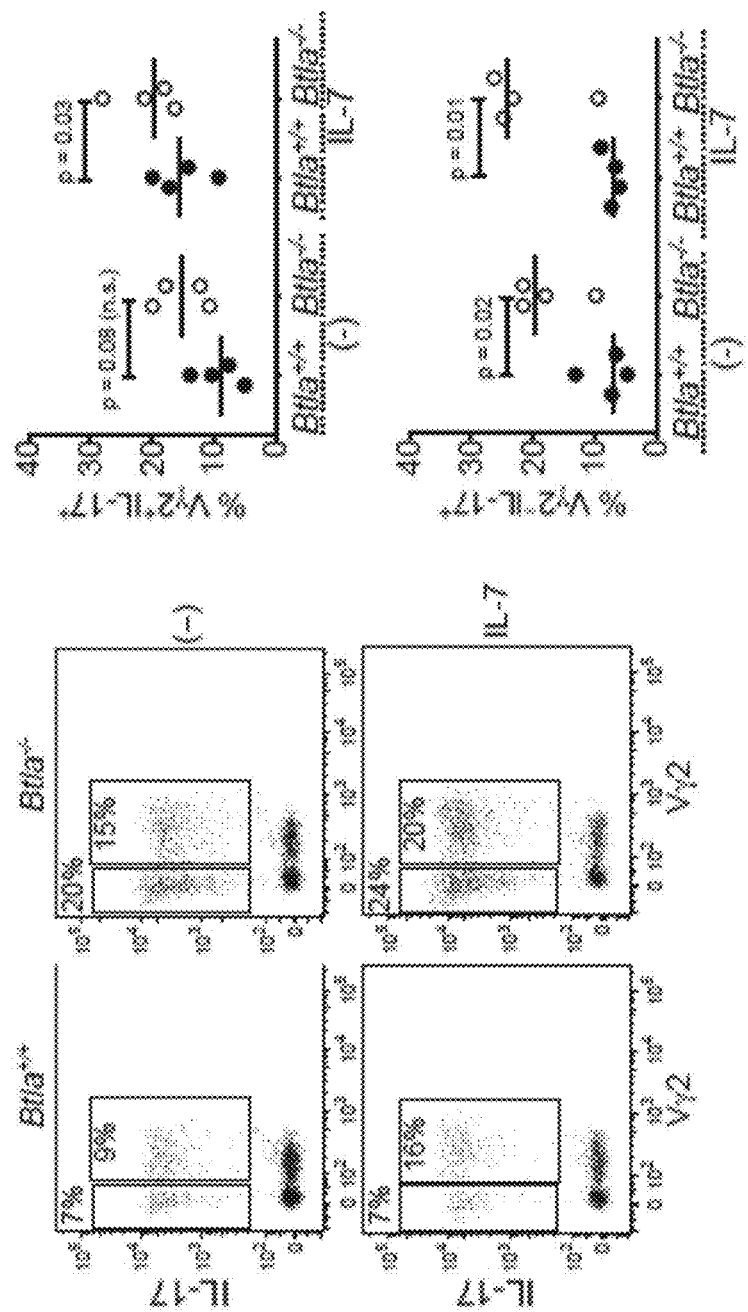
FIG. 18 shows expression of IL-17 by Vγ2$^+$ and Vγ2$^-$CD2$^-$ γδT cells by FACS and percentage.

Mature γδT cells contribute to inflammatory responses through the secretion of cytokines, IL-17 and TNF. We sought to determine whether BTLA inhibited the functionality of γδT cells stimulated with IL-7 by examining the effect on IL-17 and TNF production. As expected, among the γδT cell subsets a greater frequency of CD27 cells expressed IL-17 while more CD27$^+$ cells expressed TNF (FIG. 5). Notably, IL-7 treatment enhanced the frequency of IL-17 and TNF expressing cells in all subsets (FIG. 5). However, significantly more CD27$^-$ γδT cells from BTLA-deficient mice produced IL-17 (FIG. 5A-B) or TNF (FIG. 5C-D) compared to CD27$^-$ wild-type cells irrespective of exogenous IL-7. Moreover, there was a higher frequency of IL-17-producing Btla$^{-/-}$ γδT irrespective of Vγ2 expression (FIG. 18). Thus, BTLA negatively regulates the homeostatic, pre-programed capacity of the CD27$^-$ subset of γδT cells to produce IL-17 and TNF. In striking contrast, we observed within the CD27$^+$ subset of BTLA-deficient γδT cells an overall reduction in frequency of IL-17 and TNF expressing cells (FIG. 5). Together, these results indicate that BTLA regulates cytokine production in γδT cell subsets in a cell-specific manner independent of its effects on homeostasis.

Example 6

Figure 20C:
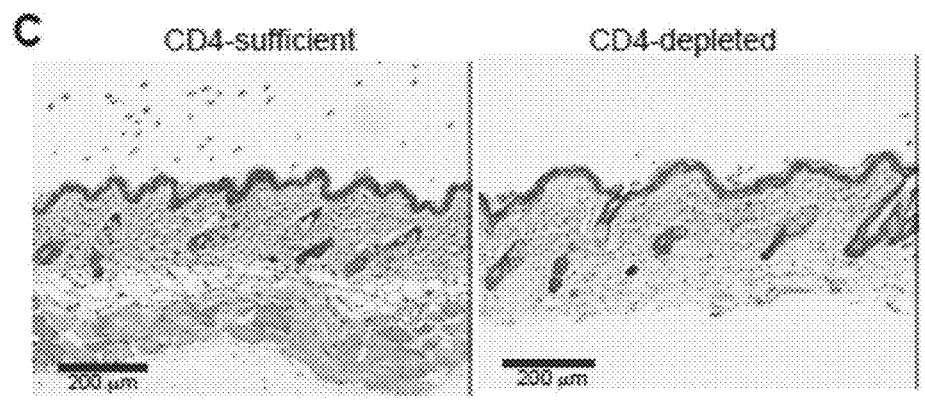

Btla$^{-/-}$ Animals are Susceptible to Dermatitis

γδT cells play critical roles in establishing skin inflammation. In mice IL-17-producing γδT cells have been shown to be the key initiators of imiquimod (IMQ)-activated psoriasis, and it was reasoned that BTLA-deficiency might confer susceptibility in this model of disease. Using an acute dermatitis induction model, substantial inflammation was observed in the skin of BTLA-deficient animals compared to minimally affected wild-type animals three days following a single dermal application of IMQ. Within the skin of IMQ-treated Btla$^{-/-}$ mice there was extensive erythema and significantly more epidermal hyperplasia (FIG. 6A-C). In addition, the number of infiltrating γδT cells that were CD27$^-$ Vγ3$^-$ (non-DETC) and expressed Vγ2, (FIG. 19) and Ly6G$^+$ granulocytes concordantly increased significantly in Btla$^{-/-}$ animals (FIG. 6D-E). Interestingly, Btla$^{-/-}$ mice showed increased skin γδT cells at steady state (FIG. 6D-E) suggesting that the absence of BTLA pre-disposes mice to skin inflammation. There was no preferential expansion of CD27$^-$ γδT cells in lymph nodes (FIG. 6F) suggesting absence of a systemic response and the presence of a localized BTLA-dependent γδT cell response. As previously shown, the response to IMQ was independent of CD4$^+$ γδT cells (FIG. 20).

Figure 21:
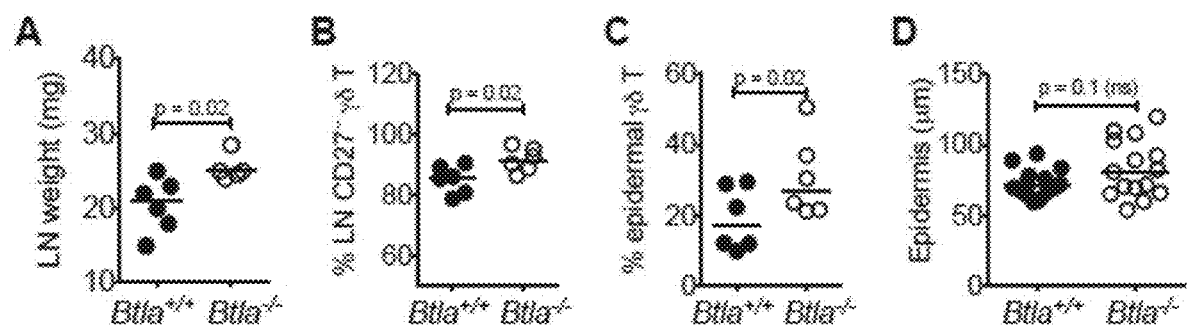
FIGS. 21A-D shows the response of wild-type and BTLA-deficient mice to daily IMQ cream application. (A) Weight of lymph nodes in IMQ-treated mice. (B) Percentage of lymph node (LN) CD2T γδT cells in IMQ-treated mice. (C) Percentage of epidermal γδT cells (TCRγδ$^+$Vγ3$^-$) in untreated or IMQ-treated mice. (D) Thickness of the epidermis in IMQ-treated mice.

However, upon repeated application of IMQ (5 days), an overwhelming inflammation occurred in both wild-type and Btla$^{-/-}$ mice obscuring any significant differences in epidermal thickness or infiltration of Ly6G-expressing granulocytes, although γδT cells increased in the skin of Btla$^{-/-}$ mice (FIG. 21C-D). In addition, enlarged lymph nodes in BTLA-deficient mice were observed compared to wild-type mice (FIG. 21A) and a higher frequency of CD27$^-$ cells (FIG. 21B), which constituted over 80% of the γδT cell population in either genetic background. This latter result indicates that the longer duration IMQ treatment resulted in a systemic response causing a greater expansion of BTLA-deficient γδT cells.

In order to directly test whether BTLA could inhibit dermatitis and inflammatory γδT cells an agonistic anti-BTLA antibody was used (clone 6A6) in wild-type animals treated with IMQ on days 1, 3, and 5, and analyzed Vγ2$^+$ CD27$^-$ γδT cell expansion and IL-17 production within lymph nodes and skin. It was found that BTLA activation inhibited the IMQ-dependent increase of γδT cells in lymph nodes and skin and significantly reduced their capacity to produce IL-17 (FIG. 7A-C). In parallel, it was observed that significantly reduced epidermal thickening in animals treated with anti-BTLA compared to control animals (FIG. 7D-E). Thus, BTLA directly limits IMQ induced skin inflammation.

Example 7

Discussion

It has been demonstrated that BTLA regulates the homeostasis of γδT cells and ILCs in lymphoid tissues. RORγt intrinsically suppresses BTLA mRNA transcription, limiting BTLA translation and membrane expression, whereas IL-7 increases BTLA membrane expression to counterbalance RORγt. These observations define BTLA as a key component in homeostasis that controls the number of innate lymphocytes in secondary lymphoid tissues. BTLA also controls IL-7-dependent proliferation and production of IL-17 and TNF in mature lymph node γδT cells. Thus, in response to inflammatory stimuli, BTLA provides a brake to autoimmune pathology that is revealed in BTLA-deficient animals, which contain a dysregulated proportion of inflammatory γδT cells, correlating with increased susceptibility to dermatitis.

The data links both the DNA and cofactor binding domains of RORγt to the repressive action on transcription of Btla. While RORγt is not known to interact with corepressors, it does interact with the coactivator Runx1 to drive IL-17 expression. However, related ROR family members RORα, RORβ, and RORγ, which regulate a variety of developmental, circadian and metabolic processes, are known to interact with the corepressors NCOR1, NCOR2, RIP140, and neuronal interacting factor in a ligand-independent fashion to repress specific gene expression. Thus, it is not unreasonable to suggest that RORγt may interact with corepressors, which act to limit the expression of additional RORγt targets. While it remains unclear how specific promoter sequences are activated or repressed by RORγt binding, this is likely a result of promoter specific cofactor recruitment. Therefore, one of the mechanisms that regulate homeostasis of CD27$^-$ γδT cells is via RORγt-dependent transcriptional down-modulation of BTLA.

The results showing BTLA regulates IL-7-dependent homeostasis of γδT cells and ILCs are consistent with previous reports that BTLA regulates homeostasis of CD8 memory T cells and splenic dendritic cell subsets. Although BTLA has not been reported to specifically regulate cytokine-induced signaling or cellular activation it was previously suggested that BTLA could regulate responses to IL-2 or other cytokines. The BTLA-binding phosphatase SHP-1 has been found to inhibit signaling initiated by IL-2 and IL-4, and likely binds directly to the cytokine receptors themselves to destabilize Janus kinase/Signal Transducer and Activator of Transcription (STAT) complexes. It is unclear whether BTLA similarly inhibits IL-7 receptor signaling, however a growing range of pathways appears susceptible to BTLA-associated tyrosine phosphatase activity including Toll-like receptor signaling. Together, these observations that IL-7 up-regulates cell surface BTLA, which then limits IL-7 receptor signaling in γδT cells, exemplifies a negative-feedback loop.

BTLA expression is likely determined by a combination of activating cytokines within the differentiating milieu. BTLA surface levels differ significantly among polarized T helper subsets. For example, in TH1 cells BTLA is highly expressed as compared to $T_H2$ cells, implicating the polarizing transcription factors GATA, STAT and T-box may be active in engaging their respective binding sites within the conserved regions of the BTLA promoter. Consistent with RORγt-dependent regulation of BTLA transcription, it was found that TH17 cells express substantially less (>2-fold) surface BTLA than non-polarized CD4$^+$ T cells. In addition to TCR signals that drive the γδT cell fate choice, CD27$^-$ RORγt$^+$γδT cells likely develop in response to IL-1/IL-23 signaling. It is unclear why specific lymphocyte subsets show different responses to BTLA activity, but one mechanism may involve subset-specific intrinsic complexes between BTLA and HVEM, or other cosignaling molecules.

γδT cells have been implicated in a variety of inflammatory diseases, supported by experimental evidence utilizing mouse autoimmune models of psoriasis, multiple sclerosis, and diabetes. The findings using a γδT cell-dependent model of inflammatory dermatitis contribute to previous data that BTLA-deficient animals are prone to the induction of autoimmune disease that in wild-type animals results in subclinical outcomes. In addition, BTLA control of early tissue-specific γδT cell associated pathology highlights the role of BTLA in regulation of innate-like cells. These results find additional relevance in recent human genome-wide association studies showing significant linkage of HVEM to autoimmune diseases including multiple sclerosis, celiac disease, sclerosing cholangitis and rheumatoid arthritis.

The susceptibility of γδT cells to inhibitory signaling makes BTLA an attractive target for selective biologics. Indeed, in several disease models, BTLA specific antibodies can alter disease progression. It was determined that BTLA is also required for optimal inflammatory cytokine production from the CD27+ γδT cell subset, potentially serving to integrate signals that sustain survival during effector and memory cell differentiation as occurs in conventional γδT cells, and perhaps in conjunction with CD27 or other costimulatory TNF receptor members. These data suggest that selective activation of BTLA may restore the balance of these pre-programmed γδT cell subsets and/or the repertoire of γδT cell specificity in order to control autoimmune pathogenesis. Collectively we demonstrate a novel molecular pathway in which RORγt and IL-7 coordinate the expression of BTLA and thus balance suppressive and activation stimuli to regulate the homeostasis and inflammatory responses of γδT cells.

It is shown here that RORγt transcriptionally represses Btla accounting for its low level of expression in CD27− RORγt+ γδT cells and ILCs. In contrast, IL-7 induces BTLA expression in γδT cells and ILCs serving to counter regulate RORγt. It is also demonstrated that BTLA limits γδT cell numbers in the thymus and is a negative regulator of γδT cell subset homeostasis in lymph nodes. The defect in homeostasis can be explained by the hyper-responsiveness of BTLA-deficient CD27− γδT cells to IL-7. Additionally, BTLA regulates the production of IL-17 and TNF in a γδT cell-subset specific manner. Furthermore, BTLA-deficient animals are susceptible to γδT cell-dependent dermatitis, while BTLA agonism limited disease. This result shows that RORγt and IL-7 form a novel regulatory circuit that impinges on BTLA to control the homeostasis and inflammatory responses of innate-like T cells.

Example 8

Methods and Materials

Mice and Mouse Cell Preparations.

Mice were bred in a C57BL/6 background and housed in the SBMRI animal facility. Rorc(t)$^{gfp/+}$, Btla$^{-/-}$, and B6.SJL-Ptprc$^a$Pep$^3$/BoyJ mice were from Jackson. Rag2$^{-/-}$ Il2rg$^{-/-}$ mice were from Taconic. Transfer of BM cell ($2\times10^6$/mouse) cells transfer was performed by intra-orbital delivery. iLN, PP or spleen cells were prepared by crushing through a 70 µm strainer. ILCs and CD27− γδT cells were enriched using the BD IMag™ system (BD Biosciences, Palo Alto, Calif.). BM cells were flushed from femurs by with PBS. Small intestinal lamina propria lymphocytes were prepared as previously described (Steinberg et al., 2008, J. Exp. Med. 205:1463).

Human Tissue and Human Cell Preparations.

Peripheral blood was obtained from healthy donors aged 18-65. Tonsils were from the NDRI. lymphocytes were prepared from heparinized blood using Ficoll (GE Healthcare, Piscataway, N.J.). Tonsil cells were isolated by digesting with collagenase D and DNaseI for 45 min.

FACS Staining.

Surface staining was performed on ice for 20-30 min. Intracellular staining was performed using the BD Cytofix/Cytoperm™ Kit according the manufacturer's instructions (BD Biosciences). Stained cells were acquired using a BD LSRFortessa™ equipped with 4 lasers (blue at 488 nm, yellow-green at 561 nm, red at 640 nm, violet at 405 nm). Antibodies in SI.

Bone Marrow Chimeras.

Wild-type animals were lethally irradiated with 900 rad and were reconstituted with $5\times10^6$ wild-type (CD45.2) mixed 1:1 with $5\times10^6$ BTLA-deficient (CD45.2+) bone marrow cells. Five weeks after reconstitution blood lymphocytes were analyzed for the presence of γδT cells.

Imiquimod Treatment and Histology.

50 mg of commercially available Aldara (5% imiquimod) cream was applied on the shaved backs of mice once or thrice every other day. Three days later animals were sacrificed and epidermal lymphocytes were prepared by incubating the tissue in 0.25% Trypsin-EDTA solution for two hours. Alternatively, mice were treated daily for five consecutive days before analysis. Anti-BTLA (6A6 clone, BioXCell, West Lebanon, N.H.) injections were performed i.p. with 100 µg antibody per mouse one day before IMQ and then a day after each IMQ application. A piece of tissue was fixed overnight in formalin for histology. Paraffin embedded sections were stained with H&E and scanned in ScanScope® XT system at 20x.

qRT-PCR.

For qRT-PCR analysis, total RNA was prepared from FACS sorted populations using the Qiagen RNeasy Mini kit according to the manufacturer's instructions (Qiagen, Valencia, Calif.). RNA was reverse transcribed into cDNA using the iScript™ cDNA synthesis kit (Bio-Rad Laboratories, Hercules, Calif.) according to the manufacturer's instructions. Target genes were detected using intron-spanning primers (Invitrogen) and relative expression was measured using Power® SYBR Master mix (Life Technologies, Grand Island, N.Y.). Reactions were carried out in clear 384 plates using an ABI® 7900 Real-Time PCR System (Life Technologies). We calculated relative expression as follows: $2^{-DCt}$, where Ct=cycle number, DCt=Ct (target gene)−Ct (house-keeping gene). A value of 1 means equal expression of target and house-keeping gene (L32). Oligo sequences (5'-3'):

```
Rorc;
                                           (SEQ ID NO: 1)
       F-ACCTCTTTTCACGGGAGGA, (SEQ ID NO: 2)
       R-TCCCACATCTCCCACATTG.

Btla;
                                           (SEQ ID NO: 3)
       F-GGGAATTCTTCATCCTCCATC, (SEQ ID NO: 4)
       R-GTTGCACTGGACACTCTTCATC.
```

Ectopic Retroviral Expression of RORγt.

HEK-293T cells were transiently co-transfected with plasmids Hit-60 (gag & pol) and VSVG (env) and either pMIG or pMIG-mRORγt (Addgene plasmid #24069) using calcium phosphate precipitation in order to produce infectious retrovirus. Supernatants were collected and used to infect the BTLA+ PE16 mouse cell line. PE16 T cell hybridoma line was derived from fusion of BW50 T thymoma cells with T cells from AND transgenic mice crossed with OX40$^{-/-}$ mice (Cheung et al., 2009, J. Immuno. 183: 7286).

Promoter Analysis.

VISTA alignments were performed online (www.genome.lbl.gov/vista) using the common RORγ-RORγt binding site using the genomic sequence of human and mouse BTLA coding genes 15 kb upstream and 1 kb downstream of the transcription start. Chromatin immuno-precipitation was performed from the RORγt-transfected PE16 T cell line with 2 µg αRORγ (Santa Cruz Biotechnology, Inc., Dallas, Tex.) or 2 µg control rabbit Ig using the SimpleChip® Kit (Cell Signaling Technology®, Danvers, Mass.). The following oligos (5'-3') were used to amplify the RORγt-bound genomic DNA:

```
RORγt site-49;
                                          (SEQ ID NO: 5)
F-CACCAGGTCTCCTGATTTGA, (SEQ ID NO: 6)
R-AGGAGTCCCAAGCATGGCA, RORγt site-369;
                                          (SEQ ID NO: 7)
F-GGTTGTAAGATACATTACACTG, (SEQ ID NO: 8)
R-TCTAAATTGTTACAGTCTTTAGG.
```

To clone the mouse Btla promoter genomic DNA was extracted from mouse tails using QuickExtract™ DNA Extraction Solution 1.0 (Epicentre, Madison, Wis.) and the 3 kb proximal BTLA promoter was amplified using Pfu II Ultra (Agilent Technologies, Inc., Santa Clara, Calif.) and the following oligos (5'-3'): F/BHI-AGTCGGATCCTG-CATGCAGTGTATCAGGAATAG (SEQ ID NO: 9), R/HIII-AGTCAAGCTTTCCCAGCACGTGTCAGG-TAAG (SEQ ID NO: 10). The product was cloned using the TOPO TA cloning kit (Life Technologies) and later was excised using BamHI (New England Biolabs, Inc., Ipswich, Mass.) and HindIII (New England Biolabs, Inc.) and ligated into the pGL4.17 luciferase construct (Promega, Madison, Wis.).

Luciferase Assay.

Jurkat cells washed in Opti-MEM® (Life Technologies) and electroporated with 10 µg or the indicated concentrations of promoter, RORγt and CD28 DNA at 230V for 65 ms using a T820 square wave electroporator (BTX®, Harvard Apparatus, Inc., Holliston, Mass.). After overnight culture in media, cells were stimulated with soluble αCD3 (5 µg/ml) and αCD28 (0.5 µg/ml) and one day later they were lysed with 1× passive lysis buffer (Promega) and assayed on a Veritas luminometer (Promega) using the Dual-Luciferase® Reporter Assay System by Promega according to the manufacturer's instructions.

Generation of RORγt and BTLA Promoter Mutants.

The RORγt truncation mutants were generated using the following oligos (5'-3') in a round-the-world PCR reaction: AF2-F-GCCTTCCCTAGCACTGATGTTGAATCCCC (SEQ ID NO: 11), AF2-R-CATCAGT-GCTAGGGAAGGCGGCTTGGAC (SEQ ID NO: 12). DBD-F-CACCTGTGAG GAAACAACTGCAACA-GCAGC (SEQ ID NO: 13), DBD-R-CAGTTGTTTC CTCACAGGTGATAACCCCG (SEQ ID NO: 14). The AF2 oligos span nucleotide positions 1429-1449 and the DBD oligos 85-293. Mutations were confirmed by sequencing. The BTLA promoter point mutations were generated using the following oligos (5'-3') in a round-the-world PCR reaction: −49-F: TGTGAATAACGtcac ggagctcTGAAGATCTCTAGGG (SEQ ID NO: 15), −49-R: CTTCAgagctccgtgaCGTTATTCACACTAGCAGCATC (SEQ ID NO: 16). −369-F: TATGAATTTCCtcac ggtgattTGATCAGAATCTAAACCTAAAG (SEQ ID NO: 17), −369-R: CTGATCAaatcaccgtgaGGAAATTCATA-CAAAAAGTACC (SEQ ID NO: 18). Lower case lettering indicates the RORγt site. In F primers bold, underlined lower case residues indicate the nucleotide substitutions (see also FIGS. 11 and 12).

In Vitro Cultures.

For IL-7 induced expansion iLN lymphocytes were cultured in RF10 media (RPMI+10% FBS, p/s, L-Glutamine) at $10^7$/ml in 12-well plates for four days. For IL-7 induced BTLA expression iLN or PP lymphocytes were enriched for ILCs and $CD27^-$ γδT cells and cultured in RF10 media in 24-well plates containing feeder adherent cells for two days. Following enrichment, cells from 3 animals were cultured in 1 ml in a single well. IL-7 (R&D Systems, Minneapolis, Minn.) was added at 10 ng/ml. For IL-17 and TNF production whole lymph node cells were cultured with or without 10 ng/ml IL-7 for 18 hours and then re-stimulated with PMA (50 ng/ml), ionomycin (750 ng/ml) and Golgi Stop™ (BD Biosciences) for 3.5 hours. TH17 differentiation was performed by isolating $CD4^+$ T cells from spleens and culturing in anti-CD3 (5 µg/ml) coated 24-well plates at $1.35 \times 10^6$/ml with anti-CD28 (2 µg/ml), IL-6 (20 ng/ml) and TGFβ1 (2 ng/ml). At day 5, cells were washed and re-stimulated with PMA+ionomycin and Golgi Stop™ (BD Biosciences) for 3.5 hours. For induction of human IL-22, tonsil lymphocytes were cultured in RF10 media at $1.5 \times 10^6$/ml in 24-well plates for 6 hours in the presence of 40 ng/ml IL-23 (eBiosciences) and 10 ng/ml IL-1β (R&D Systems). Golgi Stop™ (BD Biosciences) was added during the final 3 hours.

Statistical Analysis and Software.

All FACS data were acquired and compensated before analysis using the BD FACSDiva v6.2 software. Analysis was performed using FlowJo v9.5.2. Graphs were plotted using Prism 5.0d. 2-Way ANOVA model in R in order to perform statistical analysis was used to correct for variations in the mean fluorescent intensities (MFI) between FACS experiments. The model takes advantage of the fact that the calculations for ANOVA are the same as for linear regression and uses the following formula: lm.X=lm(Response~y1+y2, data=A), where X=a given set of data, Response=the MFI, y1=variable 1 as defined in a given FACS experiment with specific cytometer settings, y2=variable 2 defined as the two non-numerical treatment groups to be compared (e.g. γδT versus γδT cells). All other statistical analyses (comparisons of cell numbers or cell expansion) were performed using the Mann-Whitney U-test or t-test in Prism.

Antibodies to Enrich for ILCs and $CD27^-$ γδT Cells

Mouse: biotin-CD8a, CD11b, CD11c, CD19, CD27, DX5, I-Ab, Grl and Ter119. Human: biotin-CD8a, CD11 b, CD19, CD27, CD41, HLA-DR, and TCRap.

Antibodies Used for FACS Staining.

The following anti-mouse antibodies were used at different combinations for FACS staining Mouse: TCRαβ-APC-eFluor™ 780, TCRαβ-PE, TORO-PE, TCRO-APC, CD27-PECy7, TCRVγ2-PerCP-eFluor™ 710, CD127-PECy7, CD127-Alexa Fluor™ 647, BTLA-PE, HVEM-APC, DX5-FITC, CD90.2-eFluor™ 450, CD11b-PerCP-Cy5.5, CD11b-APC, CD11c-APC, B220-APC, CD45.1-FITC, IL-17A-PE, TNF-FITC, TCRVγ3-APC, Ly6G-FITC. Human: BTLA-PE, CD3-eFluor™ 450, CD117-PerCP-eFluor™ 710, IL-22-APC, CD127-APC-eFluor™ 780, CCR6-FITC, CD11b-PECy7. All antibodies were purchased from eBiosciences, San Diego, Calif. Anti-human BTLA-PE and anti-mouse IL-17A was purchased from BioLegend (San Diego, Calif.). Anti-mouse TNF-FITC was from BD Biosciences.

shRNA Knock-Down of RORγt.

The RORγt-specific siRNA 5'-ctgccagaatgaccagatt-3' (SEQ ID NO. 22) was and its complementary were annealed with the hairpin loop sequence 5'-ttcaagaga-3' (SEQ ID NO. 23) and engineered with 5' BamH1 and 3' EcoR1 restriction sites together with an internal unique Mlu1 restriction site. The annealed oligos together with negative control oligos were clones into BamH1/EcoR1 linearized pSIREN-RetroQ vector according to the manufacturer's directions (Clontech Laboratories, Inc., Mountain View, Calif.). Positive clones were identified after Mlu1 digestion. pSIREN-shRORγt or pSIREN-shControl retroviruses were produced as described in Experimental Procedure (main text) and used to create stable transfectants of PE16 cells that expressed or not RORγt. Stable transfectants were selected after two rounds of puromycin treatment followed by at least three passages after puromycin withdrawal in order to recover viable cells.

Digoxin and STAT Inhibitor Treatment.

Jurkat cells were cultured at $10^5/100$ μl in U-bottom wells for 24-48 hrs with either DMSO or the indicated concentrations of digoxin (Sigma-Aldrich). To test the effect of STAT5 in IL-7-induced BTLA expression, CD27⁻ gd T cells were enriched from lymph nodes of Rorc(t)$^{gfp/+}$ mice and cultured for two days in 24-well plates containing feeder adherent cells with no stimulus, or with IL-7 in the presence or absence of STAT inhibitor (EMD Millipore, Billerica, Mass.) at the indicated concentrations.

All references disclosed herein are incorporated herein by reference in their entirety.

Although the invention has been described with reference to the above examples, it will be understood that modifications and variations are encompassed within the spirit and scope of the invention. Accordingly, the invention is limited by the following claims.

What is claimed is:

1. A method of treating an inflammatory or autoimmune disease in a subject in need thereof comprising administering to the subject one or more agents that inhibit retinoid-related orphan receptor gamma-isoform-t (RORγt) expression or activity and/or increase IL-7 expression or activity, thereby treating the inflammatory or autoimmune disease, wherein the one or more agents is a RORγt siRNA comprising SEQ ID NO:22.

2. The method of claim 1, wherein the one or more agents increases B and T lymphocyte attenuator (BTLA) expression or activity.

3. The method of claim 1, wherein the one or more agents modulates the production of IL-17 or TNF by γδT cells.

4. The method of claim 1, wherein the one or more agents modulates the levels of RORγt⁻γδT cells or RORγt⁻γδT cells.

5. The method of claim 1, wherein one agent increases BTLA expression or activity and a second agent inhibits RORγt expression or activity.

6. The method of claim 1, wherein the one or more agents inhibits herpes virus entry mediator (HVEM)-BTLA interactions.

7. The method of claim 1, wherein the inflammatory or autoimmune disease is selected from the group consisting of psoriasis, multiple sclerosis, type I diabetes, dermatitis, celiac disease, and rheumatoid arthritis.

8. The method of claim 1, further comprising administering IL-7 to the subject.

9. A method of modulating the level and/or activity of γδT cells comprising administering an agent that modulates B- and T-lymphocyte attenuator (BTLA) expression or activity, wherein the agent increases IL-7 expression or activity or inhibits RORγt expression or activity, wherein the agent is a RORγt siRNA comprising SEQ ID NO:22.

10. The method of claim 9, wherein the agent increases BTLA expression or activity and increases the level and/or activity of γδT cells.

11. The method of claim 10, wherein the agent inhibits HVEM-BTLA interactions.

12. The method of claim 9, further comprising administering IL-7.

13. A method of modulating γδT cell production of IL-17 or TNF comprising administering an agent that modulates B- and T-lymphocyte attenuator (BTLA) expression or activity, wherein the agent increases IL-7 expression or activity or inhibits RORγt expression or activity, wherein the agent is a RORγt siRNA comprising SEQ ID NO:22.

14. The method of claim 13, wherein the agent increases BTLA expression or activity and decreases γδT cell production of IL-17 or TNF.

15. The method of claim 14, wherein the agent inhibits HVEM-BTLA interaction.

16. The method of claim 13, further comprising administering IL-7.

* * * * *

UNITED STATES PATENT AND TRADEMARK OFFICE
CERTIFICATE OF CORRECTION

PATENT NO. : 10,759,863 B2  
APPLICATION NO. : 14/916986  
DATED : September 1, 2020  
INVENTOR(S) : Ware et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 266 days.

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*